United States Patent [19]

Labeeuw et al.

[11] Patent Number: 5,523,455

[45] Date of Patent: Jun. 4, 1996

[54] SUBSTITUTED 1-NAPHTHYL-3-PYRAZOLECARBOXAMIDES WHICH ARE ACTIVE ON NEUROTENSIN, THEIR PREPARATION AND PHARMACEUTICAL COMPOSITIONS CONTAINING THEM

[75] Inventors: Bernard Labeeuw, Montpellier; Danielle Gully, Saubens; Francis Jeanjean, Valflaunes; Jean-Charles Molimard, Gely du Fesc; Robert Boigegrain, Assas, all of France

[73] Assignee: Sanofi, Paris, France

[21] Appl. No.: 442,106

[22] Filed: May 16, 1995

Related U.S. Application Data

[62] Division of Ser. No. 320,270, Oct. 11, 1994, Pat. No. 5,502,059.

[30] Foreign Application Priority Data

Oct. 12, 1993 [FR] France .................... 93 12136

[51] Int. Cl.⁶ ................................................ C07C 243/22
[52] U.S. Cl. ................ 558/418; 562/490; 564/310
[58] Field of Search ...................... 558/418; 562/490; 564/310

[56] References Cited

U.S. PATENT DOCUMENTS 5,047,422  9/1991  Junge et al. ..................... 514/510
5,288,877  2/1994  Hoelscher et al. ................ 548/490

Primary Examiner—Johann Richter
Assistant Examiner—Laura R. Cross
Attorney, Agent, or Firm—Bacon & Thomas

[57] ABSTRACT

A compound of formula:

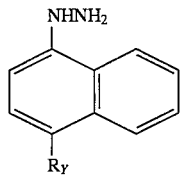

3' in which $R_y$ represents a cyano or carboxymethyl group and its salts.

2 Claims, No Drawings

SUBSTITUTED 1-NAPHTHYL-3-PYRAZOLECARBOXAMIDES WHICH ARE ACTIVE ON NEUROTENSIN, THEIR PREPARATION AND PHARMACEUTICAL COMPOSITIONS CONTAINING THEM

This application is a division of application Ser. No. 08/320,270, filed Oct. 11, 1994 now U.S. Pat. No. 5,502,059.

The present invention relates to new substituted 1-naphthyl-3-pyrazolecarboxamides having a great affinity for the human neurotensin receptor, to a process for preparing them and to pharmaceutical compositions containing them as active principles.

The first synthetic non-peptide potential medicinal products capable of binding to neurotensin receptors have been described in EP-0,477,049. They are amides of 3-pyrazolecarboxylic acid, variously substituted with amino acids, which displace iodinated neurotensin from its receptor, at doses of less than one micromole, on guinea pig brain membranes. This series led to the development of a compound, 2-[1-(7-chloro-4-quinolyl)-5-(2,6-dimethoxyphenyl)-3-pyrazolylcarbonylamino]-2-adamantanecarboxylic acid, SR 48692, endowed with potent and selective neurotensin-antagonist activity (D. Gully et al., Proc. Natl. Acad. Sci. USA, 1993, 90, 65–69).

The feature of the series of products described in EP-0,477,049 is the presence at position 1 of the pyrazole ring of, in particular, a phenyl, naphthyl or 4-quinolyl group, substituted or unsubstituted. More especially, SR 48692 possesses a 7-chloro-4-quinolyl group in position 1 of the pyrazole. The products described in this document having a 1-naphthyl or 4-chloro-1-naphthyl group in position 1 of the pyrazole ring have an extremely high affinity for the guinea pig neurotensin receptor, since their $IC_{50}$ is of the order of 1 to 10 nanomoles, whereas their affinity for the human receptor is lower since their $IC_{50}$ is from 10 to 100 nmol.

It has now been found that, by substituting position 4 of the naphthyl group of 1-naphthyl-3-pyrazolecarboxamide compounds with particular groups, the affinity for the neurotensin receptor is increased, and more especially the affinity for the human neurotensin receptor is increased.

Thus, the present invention relates, according to one of its aspects, to new substituted 1-naphthyl-3-pyrazolecarboxamides of formula:

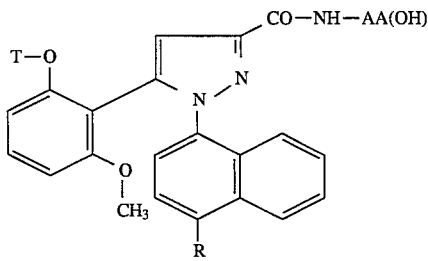

I in which:

R represents a group chosen from:
—CN, —C(NH$_2$)=N—OH, —C(NR$_4$R$_5$)=NR$_6$,
—CONR$_1$R$_2$, —CON(R$_7$)(CH$_2$)$_p$NR$_1$R$_2$,
—CON(R$_7$)(CH$_2$)$_q$CN,
—CON(R$_7$)(CH$_2$)$_q$C(NR$_{14}$R$_{15}$)=N—R$_{16}$,
—CH$_2$CN, —CH$_2$CONR$_1$R$_2$,
—CH$_2$CON(R$_7$)(CH$_2$)$_p$NR$_1$R$_2$,
—CH$_2$CON(R$_7$)(CH$_2$)$_q$CN, —CH$_2$COOR$_7$,
—O(CH$_2$)$_n$NR$_1$R$_2$, —O(CH$_2$)$_n$CONR$_1$R$_2$,
—O(CH$_2$)$_n$COOR$_7$, —O(CH$_2$)$_n$SO$_2$NR$_1$R$_2$,
—N(R$_7$)COR$_3$, —N(R$_7$)CO(CH$_2$)$_n$NR$_1$R$_2$,
—N(R$_7$)CO(CH$_2$)$_n$NHCOR$_3$, —N(R$_7$)SO$_2$R$_8$,
—N(R$_7$)CONR$_9$R$_{10}$, —CH$_2$N(R$_7$)COR$_3$,
—CH$_2$N(R$_7$)SO$_2$R$_8$, —CH$_2$CH$_2$NR$_{11}$R$_{12}$,
—CH$_2$CH$_2$N(R$_7$)COR$_3$, —CH$_2$CH$_2$N(R$_7$)SO$_2$R$_8$,
—SO$_2$NR$_1$R$_2$, —SO$_2$N(R$_7$)(CH$_2$)$_n$NR$_1$R$_2$,
—CH$_2$CON(R$_7$)(CH$_2$)$_q$C(NR$_{14}$R$_{15}$)=NR$_{16}$
—N(R$_7$)CO(CH$_2$)$_q$CN,
—N(R$_7$)CO(CH$_2$)$_q$C(NR$_{14}$R$_{15}$)=NR$_{16}$,
—SO$_2$N(R$_7$)(CH$_2$)$_q$CN,
—SO$_2$N(R$_7$)(CH$_2$)$_q$C(NR$_{14}$R$_{15}$)=NR$_{16}$,
or alternatively R, linked with the carbon atom at position 5 of the naphthyl radical, forms a group:

—CON(R$_{13}$)CO— p=2 to 6;
n=1 to 6;
q=1 to 5;

$R_1$ and $R_2$ each independently represent a hydrogen or a $(C_1$–$C_4)$ alkyl; or $R_1$ and $R_2$, together with the nitrogen atom to which they are attached, represent a heterocycle chosen from: pyrrolidine, piperidine, piperazine substituted at position 4 with $R_7$, morpholine or thiomorpholine;

$R_3$ represents hydrogen; a $(C_1$–$C_8)$ alkyl; a $(C_3$–$C_8)$ cycloalkyl; a phenyl; a piperidyl;

$R_4$ and $R_5$ each independently represent a hydrogen or a $(C_1$–$C_4)$ alkyl;

$R_6$ represents a $(C_1$–$C_4)$ alkyl;

$R_7$ represents a hydrogen or a $(C_1$–$C_4)$ alkyl;

$R_8$ represents a $(C_1$–$C_4)$ alkyl;

$R_9$ and $R_{10}$ each independently represent a hydrogen or a $(C_1$–$C_4)$ alkyl; $R_{10}$ can, furthermore, represent a group —(CH$_2$)$_n$NR$_1$R$_2$;

or $R_9$ and $R_{10}$, together with the nitrogen atom to which they are attached, represent a heterocycle chosen from: pyrrolidine, piperidine, piperazine substituted at position 4 with $R_7$, morpholine or thiomorpholine;

$R_{11}$ and $R_{12}$ each independently represent a hydrogen or a $(C_1$–$C_4)$ alkyl; or $R_{11}$ and $R_{12}$, together with the nitrogen atom to which they are attached, represent pyrrolidine or piperidine;

$R_{13}$ represents a hydrogen; a group —(CH$_2$)$_n$NR$_1$R$_2$; a group —NHCOR$_3$;

$R_{14}$ and $R_{15}$ each independently represent a hydrogen or a $(C_1$–$C_4)$ alkyl;

$R_{16}$ represents a hydrogen; $R_{16}$ can, furthermore, represent a $(C_1$–$C_4)$ alkyl when $R_{14}$ represents a hydrogen and $R_{15}$ represents a $(C_1$–$C_4)$ alkyl;

or $R_{14}$ and $R_{16}$ together represent an ethylene group or a trimethylene group and $R_{15}$ represents a hydrogen or a $(C_1$–$C_4)$ alkyl;

T represents hydrogen; a $(C_1$–$C_4)$ alkyl; an allyl; a $(C_3$–$C_8)$ cycloalkyl; a $(C_3$–$C_8)$ cycloalkylmethyl; a methoxyethyl;

the group —NH—AA(OH) represents the residue of an amino acid:

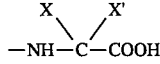

where X is hydrogen and X' is hydrogen, a $(C_1$–$C_5)$ alkyl or a non-aromatic $C_3$–$C_{15}$ carbocyclic radical; or alternatively X and X', together with the carbon atom to which they are attached, form a non-aromatic $C_3$–$C_{15}$ carbocycle;

and their salts.

Advantageously the invention relates to the compounds of formula I in which:

R represents a group chosen from:
—CN, —C(NH$_2$)=N—OH, —CONR$_1$R$_2$, —CON(R$_7$)(CH$_2$)$_p$NR$_1$R$_2$,
—O(CH$_2$)$_n$NR$_1$R$_2$, —O(CH$_2$)$_n$CONR$_1$R$_2$, —O(CH$_2$)$_n$COOR$_7$,
—O(CH$_2$)$_n$SO$_2$NR$_1$R$_2$, —NHCOR$_3$,
—NHCO(CH$_2$)$_n$NR$_1$R$_2$,
—CH$_2$CONR$_1$R$_2$, —CH$_2$CON(R$_7$)(CH$_2$)$_p$NR$_1$R$_2$,
—CH$_2$COOR$_7$,
—CH$_2$NHCOR$_3$, —SO$_2$NR$_1$R$_2$, —NHSO$_2$R$_8$,
—SO$_2$N(R$_7$)(CH$_2$)$_n$NR$_1$R$_2$,

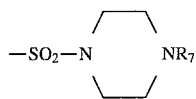

p=2 to 6;
n=1 to 6;

R$_1$ and R$_2$ each independently represent a hydrogen or a (C$_1$–C$_4$) alkyl; or R$_1$ and R$_2$, together with the nitrogen atom to which they are attached, represent a heterocycle chosen from pyrrolidine, piperidine, piperazine, morpholine or thiomorpholine;

R$_3$ represents hydrogen; a (C$_1$–C$_8$) alkyl, a (C$_3$–C$_8$) cycloalkyl, a phenyl;

R$_7$ represents a hydrogen or a (C$_1$–C$_4$) alkyl;

R$_8$ represents a (C$_1$–C$_4$) alkyl;

T represents hydrogen, a C$_1$–C$_4$ alkyl, an allyl, a C$_3$–C$_8$ cycloalkyl, a (C$_3$–C$_8$) cycloalkylmethyl, a methoxyethyl, the group —NH—AA(OH) represents the residue of an amino acid:

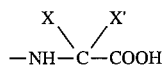

where X is hydrogen and X' is hydrogen, a C$_1$–C$_5$ alkyl or a non-aromatic C$_3$–C$_{15}$ carbocyclic radical, or alternatively X and X', together with the carbon atom to which they are attached, form a non-aromatic C$_3$–C$_{15}$ carbocycle;

and their salts.

According to the present invention, C$_1$–C$_4$ or, respectively, C$_1$–C$_5$ or, respectively, C$_1$–C$_8$ alkyl is understood to mean an unbranched or branched C$_1$–C$_4$ or, respectively, C$_1$–C$_5$ or, respectively, C$_1$–C$_8$ alkyl.

Non-aromatic C$_3$–C$_{15}$ carbocyclic radicals comprise saturated or unsaturated, fused or bridged mono- or polycyclic radicals, optionally terpenic. These radicals are optionally mono- or polysubstituted with a C$_1$–C$_4$ alkyl.

Monocyclic radicals include C$_3$–C$_{15}$ cycloalkyls, for example cyclopropyl, cyclopentyl, cyclohexyl, cycloheptyl, cyclooctyl, cyclododecyl.

In the above residue of the amino acid, when X and X', together with the carbon atom to which they are attached, form a non-aromatic C$_3$–C$_{15}$ carbocycle, the said carbocycle is as defined for the corresponding radicals above.

Among polycyclic non-aromatic carbocycles, adamantane is the preferred member, it being possible for the corresponding radical to be 1-adamantyl when X is hydrogen or 2-adamantylidene when X and X', together with the carbon atom to which they are attached, form a carbocycle.

Among monocyclic non-aromatic carbocycles, cyclopentane and cyclohexane are especially preferred.

In the formula I, R advantageously represents a group chosen from: —CONR$_1$R$_2$, —CH$_2$CONR$_1$R$_2$ and —O(CH$_2$)$_n$CONR$_1$R$_2$, the substituents R$_1$ and R$_2$ preferably being hydrogen and n preferably being 1; —N(R$_7$)COR$_3$, the substituent R$_3$ being, in particular, a (C$_1$–C$_8$) alkyl, preferably a methyl, and R$_7$ preferably being hydrogen; —CON(R$_7$)(CH$_2$)$_p$NR$_1$R$_2$, the substituent R$_7$ preferably being a hydrogen or a methyl, R$_1$ and R$_2$ both preferably being methyl and p preferably being 2, 3 or 4; and —SO$_2$N(R$_7$)(CH$_2$)$_n$NR$_1$R$_2$, the substituent R$_7$ preferably being hydrogen or methyl, R$_1$ and R$_2$ both preferably being methyl and n preferably being 2, 3 or 4; and —CON(R$_7$)(CH$_2$)$_q$C(NR$_{14}$R$_{15}$)=NR$_{16}$, the substituent R$_7$ preferably being hydrogen or methyl, R$_{14}$ and R$_{16}$ both preferably being methyl, R$_{15}$ preferably being hydrogen and q preferably being 2 or 3. Still more advantageously, at the same time, in the formula I, T represents hydrogen or a methyl or cyclopropylmethyl group. Preferably, at the same time, in the formula I, the group AA(OH) represents a 2-carboxy- 2-adamantyl or α-carboxycyclohexylmethyl radical, these two radicals representing, with the adjacent NH group, the N-terminal residues of 2-amino-2-adamantanecarboxylic acid and α-aminocyclohexaneacetic acid (cyclohexylglycine), respectively.

Preferred substituted 1-naphthyl-3-pyrazolecarboxamides according to the present invention are those of formula I in which:

R represents an aminocarbonyl; aminocarbonylmethyl; acetamido; N-[3-(N',N'-dimethylamino)propyl]aminosulphonyl; N-methyl-N-[3-(N',N'-dimethylamino)propyl]aminosulphonyl; carbamoylmethyloxy; N-[3-(N',N'-dimethylamino)propyl]aminocarbonyl; N-[2-(N',N'-dimethylamino)ethyl]aminocarbonyl; N-methyl-N-[3-(N', N'-dimethylamino)propyl]aminocarbonyl; N-methyl-N-[2-(N',N'-dimethylamino)ethyl]aminocarbonyl group; N-methyl-N[2-N$^1$-methyl-N$^2$-methylamidino)ethyl]carbamoyl;

T represents a methyl or cyclopropylmethyl group; and the group —NH—AA—(OH) represents the residue of 2-amino-2-adamantanecarboxylic or (S)-α-aminocyclohexaneacetic acid;

and their salts.

Preference attaches most especially to the compounds of formula:

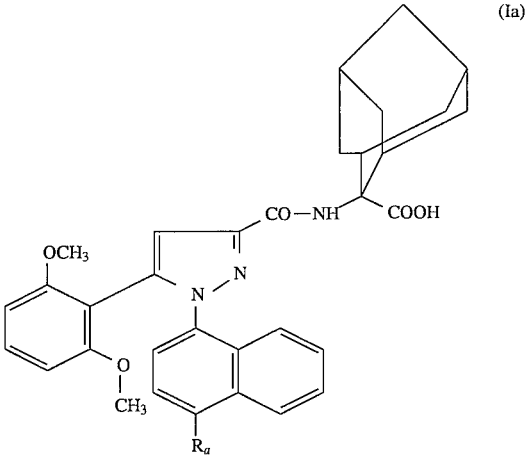

in which

R$_a$ represents an N-[3-(N',N'-dimethylamino)propyl]aminocarbonyl or N-[2-(N',N'-dimethylamino)ethyl]aminocarbonyl group;

and their salts.

The salts of the invention compounds are those with alkali metals, preferably sodium or potassium, and alkaline-earth metals, preferably calcium, and with organic bases such as diethylamine, tromethamine, meglumine (N-methyl-D-glucamine), lysine, arginine, histidine or diethanolamine.

The salts of the compounds of formula I according to the present invention also comprise those with inorganic or organic acids which permit an appropriate separation or crystallization of the compounds of formula I, such as picric acid, oxalic acid or an optically active acid, for example a mandelic acid or a camphorsulphonic acid, and those which form pharmaceutically acceptable salts such as the hydrochloride, hydrogen sulphate, dihydrogen phosphate, methanesulphonate, maleate, fumarate, 2-naphthalenesulphonate and isethionate.

When the compounds I include an asymmetric carbon, the enantiomers form part of the invention.

When the group —NH(AA)OH represents the residue of a cycloaliphatic amino acid, the amino or aminomethyl groups can be in the endo position or in the exo position with respect to the ring-system; in both cases, the compounds of formula I form part of the invention.

According to another of its aspects, the present invention relates to a process for the preparation of the substituted 1-naphthyl-3-pyrazolecarboxamides of formula I and their salts, characterized in that:

1) a functional derivative of a 1-naphthyl-3-pyrazolecarboxylic acid of formula:

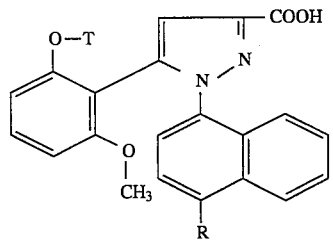

II or

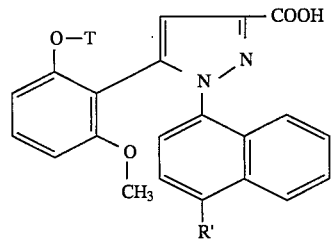

II' in which T and R have the meanings given above for the compound of formula I and R' represents a precursor of R chosen from nitro, amino, hydroxyl, sulpho, chlorosulphonyl and carboxyl groups, is treated with an amino acid, optionally protected by protective groups which are customary in peptide synthesis, of formula:

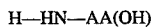   III in which —NH—AA(OH) is as defined above for the compound of formula I;

2) where appropriate, the compound thereby obtained, of formula:

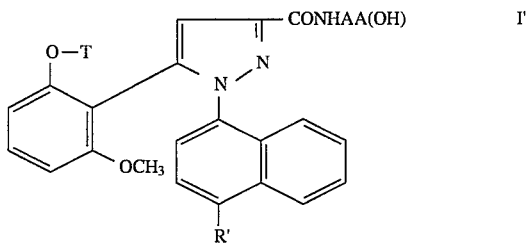

I' is subjected to a subsequent treatment suitable for converting the substituent R', a precursor of R, to the substituent R;

3) if necessary, the compound thereby obtained in step 1) or in step 2) is deprotected to yield the corresponding free acid of formula I;

4) where appropriate, a salt is prepared of the compound I thereby obtained.

As a functional derivative of the substituted 1-naphthyl-3-pyrazolecarboxylic acid of formula II or II', it is possible to use the acid chloride, the anhydride, a mixed anhydride, a $C_1$–$C_4$ alkyl ester, an activated ester, for example the p-nitrophenyl ester, or the free acid appropriately activated, for example with N,N-dicyclohexylcarbodiimide or with benzotriazol-1-yloxytris(dimethylamino)phosphonium hexafluorophosphate (BOP).

The amino acids of formula III may be used either as they are, or after prior protection of the carboxyl group with protective groups which are customary in peptide synthesis, as described, for example, in Protective Groups in Organic Chemistry, Ed. J. F. W. McOmie, Plenum Press, 1973, page 183, or in Protective Groups in Organic Synthesis, II Ed. J. F. W. Greene and P. G. M. Wuts, John Wiley & Sons, 1991, page 224.

For this protection, the carboxyl group of the amino acid III may be quite simply esterified, for example in the form of the methyl, isobutyl or tertbutyl ester, the esterifying group then being removed by saponification or reduction. Protection by esterification can be used only when the group R or R' does not contain, for its part also, either an ester group which must be preserved, as in the case where, for example, R might represent a group $O(CH_2)_n COOR_7$ or $CH_2COOR_7$ with $R_7$=alkyl, or, in any case, a group liable to be effected during the unblocking of the ester group. Protection of the carboxyl group of the amino acid III may also be performed by silylation, for example with bis(trimethylsilyl)acetamide, it being possible for the said protection to be performed in situ. The silyl ester of the compound I is then readily decomposed during the isolation of the final product by simple acidification.

Thus, in step 1) of the process, the chloride of a 1-naphthyl-3-pyrazolecarboxylic acid, obtained by reacting thionyl chloride or oxalyl chloride with an acid of formula II or II', may be reacted with an amino acid of formula III, in a solvent such as acetonitrile, THF, DMF or DCM, under an inert atmosphere, at room temperature, for a time between a few hours and a few days, in the presence of a base such as pyridine, sodium hydroxide or triethylamine.

A variant of step 1) consists in preparing the acid chloride or the mixed anhydride of a 1-naphthyl-3-pyrazolecarboxylic acid by reacting isobutyl or ethyl chloroformate with an acid of formula II or II', in the presence of a base such as triethylamine, and in reacting it with an N,O-bis(trimethylsilyl) derivative of an amino acid of formula III, obtained by reacting bis(trimethylsilyl)acetamide or 1,3-bis(trimethylsilyl)urea with an amino acid of formula III, in solvents such as acetonitrile or DCM, under an inert atmosphere, at room temperature, for a time between 1 day and a few days.

Another variant to the procedure of step 1) consists in reacting the mixed anhydride of a 1-naphthyl-3-pyrazole-carboxylic acid of formula II or II' with an amino acid of formula III, in a solvent such as DCM, under an inert atmosphere, at room temperature, for a time between 1 day and a few days, in the presence of a base such as triethylamine.

When the compound of formula I possesses a basic function and is obtained in the form of a free base, salification is performed by treatment with the chosen acid in an organic solvent. By treatment of the free base, dissolved, for example, in an alcohol such as methanol, with a solution of the chosen acid in the same solvent or another solvent such as ethyl ether, the corresponding salt is obtained, which salt is isolated according to standard techniques. Thus, for example, the hydrochloride, hydrobromide, sulphate, hydrogen sulphate, dihydrogen phosphate, methanesulphonate, methyl sulphate, oxalate, maleate, fumarate, 2-naphthalenesulphonate or isethionate is prepared.

When the compound of formula I possesses a basic function and is isolated in the form of one of its salts, for example the hydrochloride or oxalate, the free base may be prepared by neutralization of the said salt with an inorganic or organic base such as sodium hydroxide or triethylamine, or with an alkali metal carbonate or bicarbonate such as sodium or potassium carbonate or bicarbonate.

When the product of formula I is obtained in acid form, it may be converted to a metal salt, in particular an alkali metal salt such as the sodium salt or an alkaline-earth metal salt such as the calcium salt, according to standard processes.

The substituted 1-naphthyl-3-pyrazolecarboxylic acids of formula:

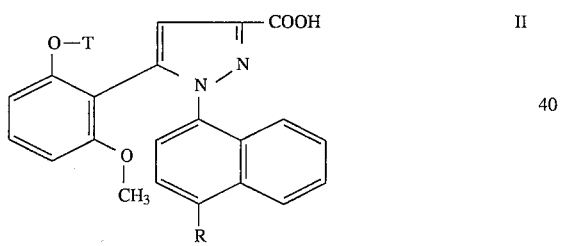

II or

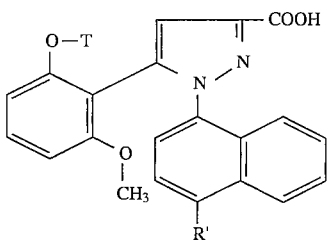

II' in which T and R have the definitions given above for the compounds I and R' represents a precursor of R chosen from nitro, amino, hydroxyl, sulpho, chlorosulphonyl and carboxyl groups, as well as their functional derivatives of the acid function, are key intermediates in the preparation of the compounds of formula I. When R' is other than carboxyl, the compounds of formulae II and II' are new and they constitute a further aspect of the present invention.

The acids of formulae II and II', the chlorides of the acids of formulae II and II', the $C_1$–$C_4$ alkyl esters of the acids of formulae II and II', which can also be precursors of the said acids (in particular the methyl, ethyl and t-butyl esters), and the mixed anhydride of the acids of formulae II and II' with isobutyl or ethyl chloroformate are especially preferred intermediate products.

The process for preparing the compounds II or II' via the esters IIa or II'a is represented by the following scheme:

SCHEME 1

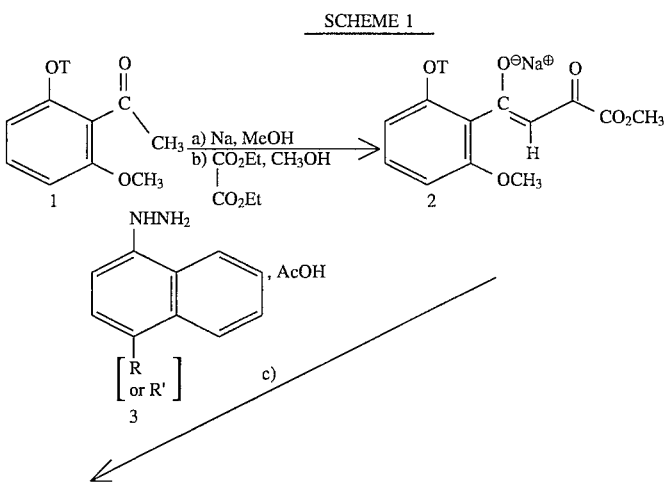

-continued
SCHEME 1

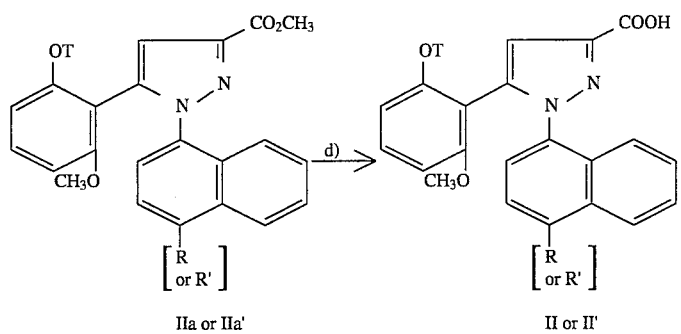

IIa or II'a          II or II'

In the first step a), a strong base such as sodium methylate is reacted with a ketone of formula 1 in which T is as defined above, and an equimolar amount of ethyl oxalate in an alkanol such as, for example, methanol is then reacted (step b)) according to L. Claisen, Ber., 1909, 42, 59. After precipitation in an ether such as ethyl ether or isopropyl ether, the sodium enolates 2 are separated by filtration. It is also possible to prepare a lithium enolate according to W. V. Murray et al., J. Heterocyclic Chem., 1989, 26, 1389.

The metal enolate 2 thus prepared and an excess of naphthylhydrazine derivative 3, or of a salt of the latter, are then heated to reflux of acetic acid (step c)) to obtain the esters IIa or II'a.

By saponification of the esters IIa or II'a by the action of an alkaline agent such as, for example, potassium hydroxide, sodium hydroxide or lithium hydroxide, followed by acidification, the acids II or II' are obtained (step d)).

In a particular case, a compound of formula II in which R, linked with the carbon atom at position 5 of the naphthyl radical, forms a group —CO—N($R_{13}$)CO— with $R_{13}$=—NHCOR$_3$, is prepared using the process illustrated in Scheme 2 below:

SCHEME 2

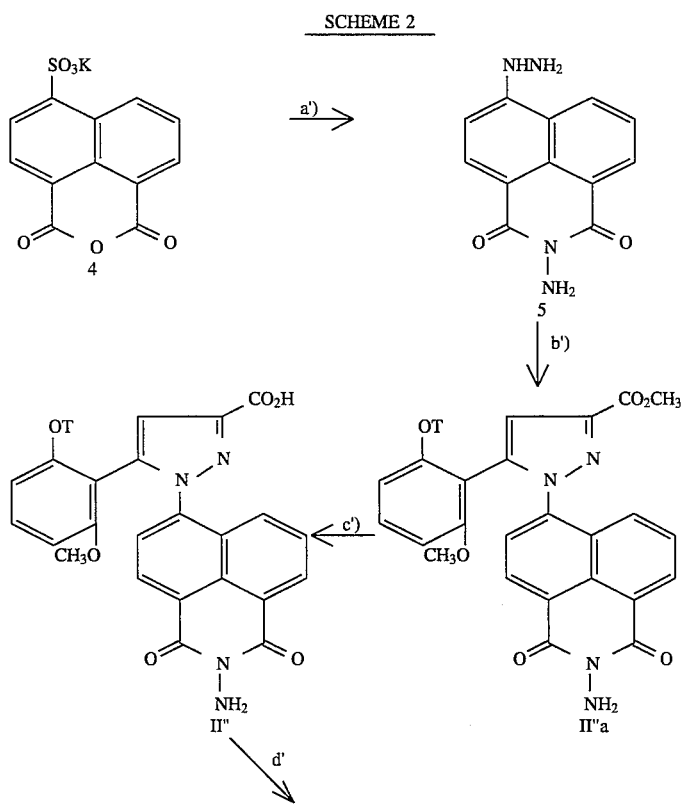

-continued
SCHEME 2

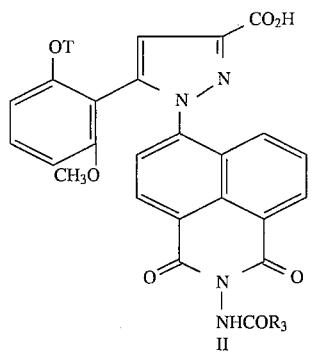
II

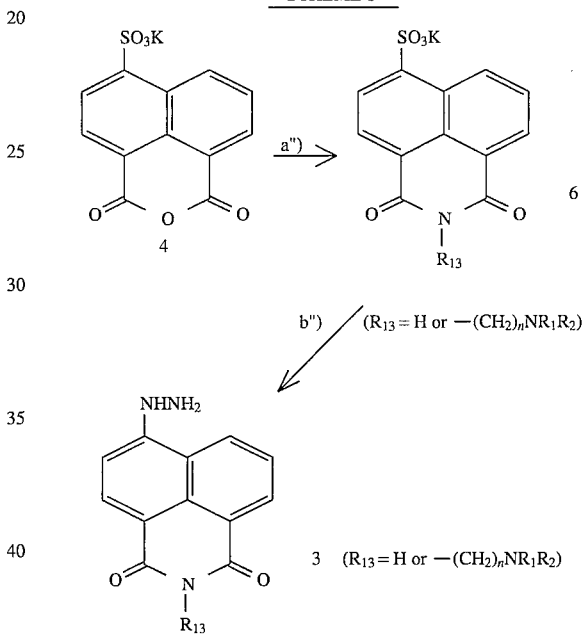

SCHEME 3

In the first step a'), the potassium salt of 4-sulpho-1,8-naphthalic anhydride is reacted with hydrazine monohydrate by heating to a temperature of 120° C. for 36 hours. After precipitation in water, the compound 5 is separated by filtration. Reaction of the hydrazine 5 with the metal enolate 2 (step b') according to the process described in step c) of Scheme 1 enables the esters II"a to be obtained. By saponification of the esters II"a (step c') according to the process described in step d) of Scheme 1, the acids II" are obtained. By reaction of the acids II" with suitable acid chlorides or anhydrides, the expected compounds II are obtained.

Some of the compounds of formula 3 are new and are a further object of the present invention. Thus, the compounds of formula:

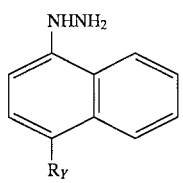

3' in which:

$R_y$ represents a cyano or a carboxymethyl group and their salts are novel and within the scope of the present invention.

The naphthylhydrazine derivatives (3) bearing a substituent R or a substituent R' may be prepared by diazotization of the corresponding naphthylamine in the presence of sodium nitrite, followed by reduction of the diazonium salt, for example by the action of stannous chloride. The substituted naphthylamines are known or prepared by known methods.

The naphthylhydrazine derivatives in which R, linked with the carbon atom at position 5 of the naphthyl radical, forms a group $-CON(R_{13})CO-$, with $R_{13}=H$ or $-(CH_2)_nNR_1R_2$, are prepared using the process illustrated in Scheme 3 below:

Reaction of the compound 4 with an amine of formula $H_2NR_{13}$ in which $R_{13}$ is hydrogen or a group $-(CH_2)_nNR_1R_2$ enables the compounds 6 to be obtained (step a"). By heating the compounds 6 with hydrazine monohydrate in aqueous solution, the expected hydrazines 3 are obtained (step b").

The conversion of a compound of formula I' or, respectively, of formula II' or formula II'a in which the naphthyl group is substituted with R' to a compound of formula I or, respectively, of formula II or formula IIa in which the naphthyl group is substituted with R is performed by standard methods well known to a person skilled in the art.

For example, when $R'=SO_3H$, a compound II'a in which $R'=SO_2Cl$ is prepared, and is then converted to another compound IIa, in which R is an optionally substituted aminosulphonyl group, by the action of a suitable amine of formula $NHR_1R_2$, $HN(R_7)(CH_2)_nNR_1R_2$ or $HN(R_7)(CH_2)_qCN$ in which $R_1$, $R_2$, $R_7$, n and q have the definition given above for the compound of formula I.

The compounds of formula IIa in which R represents a carboxymethyl group enable compounds of formula IIa in which R represents a group $-CH_2CONR_1R_2$ or, respectively, a group $-CH_2CON(R_7)(CH_2)_pNR_1R_2$ or a group $-CH_2CON(R_7)(CH_2)_qCN$ to be prepared by reacting the acid chloride, prepared as an intermediate, with an amine $HNR_1R_2$ or, respectively, with a diamine $HN(R_7)(CH_2)_pNR_1R_2$ or with an amino compound $HN(R_7)(CH_2)_qCN$.

By reacting the compounds of formula I in which R represents a —$CH_2CONH_2$ group with sodium peroxide, the compounds of formula I in which R represents a carboxymethyl group are obtained. During the preparation of the compounds of formula I in which R represents a —$CH_2CONH_2$ group from the compounds of formula II in which R represents a —$CH_2CONH_2$ group, the compounds of formula I in which R represents a —$CN_2CN$ group are also obtained, which compounds are separated by chromatography. By reduction of the compounds of formula I in which R represents a —$CH_2CN$ group, for example by hydrogenation in the presence of a catalyst such as Raney® nickel, the compounds of formula I in which R represents a —$CH_2CH_2NH_2$ group are obtained. These latter compounds enable compounds of formula I in which R represents a group —$CH_2CH_2NR_1R_2$, a group —$CH_2CH_2N(R_7)COR_3$, a group —$CH_2CH_2N(R_7)SO_2R_8$ to be prepared by methods known to a person skilled in the art.

The compounds of formula II'a or, respectively, the compounds of formula II' or the compounds of formula I' in which R' represents a nitro group may be converted to the compounds of formula II'a or, respectively, of formula II' or formula I' in which R' is an amino group; then, by known methods, the compounds of formula IIa or, respectively, of formula II or formula IIa in which R represents a group —$N(R_7)COR_3$, a group —$N(R_7)CO(CH_2)_nNR_1R_2$, a group —$N(R_7)CO(CH_2)_nNHCOR_3$, a group —$N(R_7)SO_2R_8$, a group —$N(R_7)CONR_9R_{10}$ or a group —$N(R_7)CO(CH_2)_qCN$ are prepared.

The compounds of formula II'a or, respectively, of formula II' or formula I' in which R' is an amino group also enable compounds of formula II'a or, respectively, of formula II' or formula I' in which R' represents a hydroxyl group to be prepared; then, by known methods, the compounds of formula IIa or, respectively, of formula II or formula I in which R represents a group —$O(CH_2)_nNR_1R_2$, a group —$O(CH_2)_nCONR_1R_2$, a group —$O(CH_2)_nCOOR_7$ or a group —$O(CH_2)_nSO_2NR_1R_2$ are prepared.

The compounds of formula I in which R is a cyano group enable the compounds of formula I in which R is a carbamoyl group to be prepared by reaction with hydrogen peroxide in the presence of a base such as sodium hydroxide. Likewise, the compounds of formula II in which R is a carbamoyl group are obtained from the compounds of formula IIa In which R is a cyano group.

The compounds of formula I in which R is a cyano group also enable the compounds of formula I in which R represents a —$C(NH_2)$=NOH group to be prepared, by reaction with hydroxylamine in the presence of a base such as potassium carbonate.

By reduction of the compounds of formula IIa or, respectively, of formula II or formula I in which R represents a cyano group, for example by hydrogenation in the presence of a catalyst such as platinum oxide, followed by reaction with a suitable acid chloride or anhydride or, respectively, with a sulphonyl chloride, the compounds of formula IIa or, respectively, of formula II or formula I in which R represents a group —$CH_2NHCOR_3$ or, respectively, —$CH_2NHSO_2R_8$ are obtained. Similarly, the compounds of formula IIa or, respectively, of formula II or formula I in which R represents a group —$CH_2N(R_7)COR_3$ or a group —$CH_2N(R_7)SO_2R_8$ with $R_7$ other than hydrogen, are obtained by performing an alkylation reaction on the amine obtained as an intermediate.

The compounds of formula II'a in which R' represents a carboxyl group enable the compounds of formula IIa in which R represents a group —$CONR_1R_2$ or, respectively, a group —$CON(R_7)(CH_2)_pNR_1R_2$ or a group —$CON(R_7)(CH_2)_qCN$ to be prepared by reacting the acid chloride, prepared as an intermediate, with an amine $HNR_1R_2$ or, respectively, with an amine $HN(R_7)(CH_2)_pNR_1R_2$ or with an amine $HN(R_7)(CH_2)_qCN$.

Reaction of the compounds of formula I in which R represents a group —$CON(R_7)(CH_2)_qCN$, a group —$CH_2CON(R_7)(CH_2)_qCN$, a group —$N(R_7)CO(CH_2)_qCN$ or a group —$SO_2N(R_7)(CH_2)_qCN$ with hydrochloric acid in alcoholic solution enables the corresponding imidate to be obtained as an intermediate. If the imidate is reacted with an equimolar amount of amine $HNR_{14}R_{15}$, the compounds of formula I in which R represents a group —$CON(R_7)(CH_2)_qC(NR_{14}R_{15})$=$NR_{16}$, a group —$CH_2CON(R_7)(CH_2)_qC(NR_{14}R_{15})$=$NR_{16}$, a group —$N(R_7)CO(CH_2)_qC(NR_{14}R_{15})$=$NR_{16}$ or a group —$SO_2N(R_7)(CH_2)_qC(NR_{14}R_{15})$=$NR_{16}$ with $R_{16}$=H, are obtained. If the imidate is reacted with an excess of amine $HNR_{14}R_{15}$, the compounds of formula I in which R represents a group —$CON(R_7)(CH_2)_qC(NR_{14}R_{15})$=N—$R_{16}$, a group —$CH_2CON(R_7)(CH_2)_qC(NR_{14}R_{15})$=$NR_{16}$, a group —$N(R_7)CO(CH_2)_qC(NR_{14}R_{15})$=$NR_{16}$ or a group —$SO_2N(R_7)(CH_2)_qC(NR_{14}R_{15})$=$NR_{16}$ with $R_{16}$ other than hydrogen, are obtained. If the imidate is reacted with ethylenediamine, unsubstituted or N-substituted with a ($C_1$–$C_4$) alkyl, or with 1,3-diaminopropane, unsubstituted or N-substituted with a ($C_1$–$C_4$) alkyl, the compounds of formula I in which R represents a group —$CON(R_7)(CH_2)_qC(NR_{14}R_{15})$=N—$R_{16}$, a group —$CH_2CON(R_7)(CH_2)_qC(NR_{14}R_{15})$=$NR_{16}$, a group —$N(R_7)CO(CH_2)_qC(NR_{14}R_{15})$=$NR_{16}$ or a group —$SO_2N(R_7)(CH_2)_qC(NR_{14}R_{15})$=$NR_{16}$, in which $R_{14}$ and $R_{16}$ together constitute an ethylene or trimethylene group and $R_{15}$ represents a hydrogen or a ($C_1$—$C_4$) alkyl, are obtained.

The compounds of formula I in which R represents a carbamoyl group monosubstituted on the nitrogen enable the compounds of formula I in which R represents a group —$C(NR_4R_5)$=N—$R_6$ to be prepared by reaction with phosphorus pentachloride followed by reaction with an amine $HNR_4R_5$.

The amino acids of formula III include, for example, glycine, alanine, leucine, norleucine, isoleucine, valine, 1-adamantylglycine, 2-adamantylglycine, cyclopropylglycine, cyclopentylglycine, cyclohexylglycine, cycloheptylglycine, 1-aminocyclopropanecarboxylic acid, 1-aminocyclobutanecarboxylic acid, 1-aminocyclopentanecarboxylic acid, 1-aminocyclohexanecarboxylic acid, 1-aminocycloheptanecarboxylic acid, 1-amino- 4-methylcyclohexanecarboxylic acid, 2-amino-2-adamantanecarboxylic acid, 2-aminobicyclo[3.2.1]octane- 2-carboxylic acid, 9-aminobicyclo[3.3.1]nonane-9-carboxylic acid and 2-aminobicyclo[2.2.1]heptane-2-carboxylic (or 2-amino-2-norbornanecarboxylic) acid.

The amino acids of formula III are commercial products or may be very readily prepared according to standard methods. In particular, the non-commercial amino acids (III) are prepared according to the Strecker synthesis, Ann, 1850, 75, 27 or according to the synthesis of H. T. Bucherer et al., J. Pract. Chem., 1934, 141, 5, followed by a hydrolysis to yield the amino acids; for example, 2-amino-2-adamantanecarboxylic acid is prepared according to H. T. Nagasawa et al., J. Med. Chem., 1973, 16, (7), 823.

α-Amino-1-adamantylacetic and α-amino-2-adamantylacetic acids are prepared according to B. Gaspert et al., Croatica Chemica Acta, 1976, 48 (2), 169–178.

2-Amino-2-norbornanecarboxylic acid is prepared according to H. S. Tager et al., J. Am. Chem. Soc., 1972, 94, 968.

α-Aminocycloalkylcarboxylic acids are prepared according to J. W. Tsang et al., J. Med. Chem., 1984, 27, 1663.

(R)- and (S)-cyclopentylglycines are prepared according to European Patent Application EP 477,049.

(R)- and (S)-cyclohexylglycines are prepared according to Rudman et al., J. Am. Chem. Soc., 1952, 74, 551.

(R)- and (S)-cyclohexylglycines may also be prepared by catalytic hydrogenation of (R)- and (S)-phenylglycines.

α-Aminocycloalkylcarboxylic acids of R or S configuration may also be prepared by stereospecific enzymatic hydrolysis of the corresponding racemic N-acetyl derivatives according to J. Hill et al., J. Org. Chem., 1965, 1321.

The compounds of formula I and their salts possess a very great affinity for human neurotensin receptors in the tests described in the publication of D. Gully et al. cited above. More especially, relative to the 1-naphthyl and 4-chloro-1-naphthyl derivatives described in EP 0,477,049, which have an $IC_{50}$ equal to or greater than 100 nM, the compounds of the invention possess a markedly lower $IC_{50}$, ranging from 1 nM to 50 nM. Special importance attaches to the products of formula I in which T is methyl and R is aminocarbonyl; aminocarbonylmethyl; acetamido; N-methyl-N-[3-(N',N'-dimethylamino)propyl]aminosulphonyl; carbamoylmethyloxy; N-[3-(N',N'-dimethylamino)propyl]aminocarbonyl; N-[2-(N',N'-dimethylamino)ethyl]aminocarbonyl. These compounds are hence even more active than SR 48692, which is unexpected if reference is made to the activity of the 1-naphthyl-3-pyrazolecarboxamides described in EP 0,477,049.

The compounds of formula I and their salts were studied in vivo. Working according to the technique described by M. Poncelet et al. in Naunyn Schmiedberg's Arch. Pharmacol., 1994, 60, 349–357, it is observed that the compounds according to the invention, administered orally, antagonize the contralateral pivoting induced by unilateral intrastriatal injection of neurotensin in mice.

Moreover, working according to the technique described by D. Nisato et al. in Life Sciences, 1994, 54, 7, 95–100, it is found that the compounds according to the invention, administered intravenously, inhibit the increase in blood pressure induced by intravenous injection of neurotensin in anaesthetized guinea pigs.

The compounds described in Patent EP 0,477,049 exhibit a lower activity in these tests than that of the compounds according to the present invention.

The compounds of the present invention and their pharmaceutically acceptable salts are of low toxicity; in particular, their acute toxicity is compatible with their use as a medicinal product. For such a use, an effective amount of a compound of formula I, or of one of its pharmaceutically acceptable salts, is administered to mammals for the treatment of neurotensin-dependent pathologies. Thus, the compounds of the present invention may be used for the treatment of neuropsychiatric disorders, especially those associated with a dysfunction of the dopaminergic systems, for example psychoses, more especially schizophrenia and diseases of movement such as Parkinson's disease (D. R. Handrich et al., Brain Research, 1982, 231, 216–221 and C. B. Nemeroff, Biological Psychiatry, 1980, 15 (2), 283–302). They may be used to diagnose and/or treat malignant neoplastic diseases, for example human meningiomas which are not surgically accessible (P. Mailleux, Peptides, 1990, 11, 1245–1253), cancers of the prostate (I. Sehgal et al., Proc. Nat. Acad. Sci., 1994, 91, 4673–4677) and small cell cancers of the lung (T. Sethi et al., Cancer Res., 1991, 51, 3621–3623). They may be used in the treatment of motor, secretory, ulcerous and/or tumoral gastrointestinal disorders (review by A. Shulkes in "Gut Peptides: Biochemistry and Physiology, Ed. J. Waish and G. J. Dockray, 1994"). Thus, the compounds I according to the invention may be used in the treatment of complaints such as: irritable bowel syndrome, diarrhoea, colitis, ulcers, tumours of the gastrointestinal tract, dyspepsia, pancreatitis and oesophagitis. The compounds according to the invention may be indicated in the case of cardiovascular disorders, and also in the case of pathologies associated with a histamine release such as inflammatory processes (D. E. Cochrane et al., Faseb J., 1994, 8, 7, 1195). The compounds of the present invention may also be of value in analgesia, by acting on the effects of morphine (M. O. Urban, J. Pharm. Exp. Ther., 1993, 265, 2, 580–586).

Thus, the subject of the present invention, according to another of its aspects, is pharmaceutical compositions containing as active principles the compounds of formula I or their possible pharmaceutically acceptable salts.

In the pharmaceutical compositions of the present invention for oral, sublingual, subcutaneous, intramuscular, intravenous, transdermal or rectal administration, the active principles may be adminisered, in single-dose administration forms, as a mixture or with standard pharmaceutical vehicles, to animals and human beings. Suitable single-dose administration forms comprise forms for oral administration, such as tablets, gelatin capsules, powders, granules and oral solutions or suspensions, forms for sublingual and buccal administration, forms for subcutaneous, intramuscular or intravenous administration and forms of rectal administration.

In order to obtain the desired effect, the dose of active principle can vary between 0.5 and 1000 mg per day, and preferably between 2 and 500 mg.

Each single dose can contain from 0.5 to 250 mg of active principle, and preferably from 1 to 125 mg, in combination with a pharmaceutical vehicle. This single dose can be administered 1 to 4 times daily.

When a solid composition is prepared in the form of tablets, the active principle is mixed with a pharmaceutical vehicle such as gelatin, starch, lactose, magnesium stearate, talc, gum arabic or the like. It is possible to coat the tablets with sucrose or with other suitable substances, or they may alternatively be treated in such a way as to have a sustained or delayed activity and to release continuously a predetermined amount of active principle.

A gelatin capsule preparation is obtained by mixing the active principle with a diluent and pouring the mixture obtained into soft or hard gelatin capsules.

A preparation in syrup or elixir form can contain the active principle together with a sweetener, preferably a zero-calorie sweetner, and methylparaben and propylparaben as antiseptic, as well as an agent imparting flavour and a suitable colorant.

The water-dispersible powders or granules can contain the active principle mixed with dispersing agents or wetting agents, or suspending agents, such as polyvinylpyrrolidone and the like, as well as with sweeteners or flavour correctors.

For rectal administration, suppositories are employed, which are prepared with binding agents melting at rectal temperature, for example cocoa butter or polyethylene glycols.

For parenteral administration, aqueous suspensions, isotonic saline solutions or sterile and injectable solutions are used, which contain pharmacologically compatible dispersing and/or wetting agents, for example propylene glycol or butylene glycol.

The active principle may also be formulated in the form of microcapsules, optionally with one or more vehicles or additives.

To improve the solubility of the products of the invention, the compounds of formula I or their pharmaceutically acceptable salts may also be presented in the form of complexes with cyclodextrins.

In the description and in the examples, the following abbreviations are used:

MeOH: methanol
EtOH: ethanol
Ether: ethyl ether
Iso ether: isopropyl ether
AcOEt: ethyl acetate
MeCN: acetonitrile
DCM: dichloromethane
DMF: dimethylformamide
DMSO: dimethyl sulphoxide
THF: tetrahydrofuran
HCl: hydrochloric acid
AcOH: acetic acid
TFA: trifluoroacetic acid
$H_2SO_4$: sulphuric acid
NaOH: sodium hydroxide
KOH: potassium hydroxide
$NH_4OH$: aqueous ammonia
$Na_2SO_4$: sodium sulphate
$P_2O_5$: phosphorus pentoxide
Me, MeO: methyl, methoxy
Et: ethyl
M.p.: melting point
RT: room temperature
Silica H: silica gel 60 H marketed by MERCK (DARMSTAD)
NMR: nuclear magnetic resonance
s: singlet
bs: broad singlet
d: doublet
t: triplet
qr: quartet
qt: quintet
u.c.: unresolved complex
mt: multiplet

PREPARATION 1

Methyl 4-(2,6-dimethoxyphenyl)-4-oxido-2-oxo-3-butenoate Sodium Salt

A solution of 100 g of 2,6-dimethoxyacetophenone and 7.5 ml of ethyl oxalate in 520 ml of anhydrous MeOH is added slowly to a solution of sodium methylate prepared from 12.7 g of sodium and 285 ml of anhydrous MeOH. The reaction mixture is heated to reflux for 7 hours and left overnight at RT. It is poured into 2 liters of iso ether and left stirring for minutes. The expected product is obtained by filtration, washing with iso ether and drying under vacuum, m=120 g, m.p.=178° C.

PREPARATIONS OF THE HYDRAZINES 3

Preparation 2.1

1-Hydrazino-4-nitronaphthalene Hydrochloride

A solution of 1.9 g of sodium nitrite in 10 ml of water is added to a suspension, cooled to −5° C., of 5.2 g of 4-nitro-1-naphthylamine in 150 ml of concentrated HCl, 100 ml of 1N HCl and 150 ml of AcOH. The mixture is left stirring for 1 hour 15 minutes at a temperature of between −5° C. and 0° C. It is cooled to −15° C., and a solution of 12.5 g of stannous chloride dihydrate in 30 ml of concentrated HCl is added very slowly. The temperature is allowed to rise to RT and the reaction mixture is kept stirring for 2 hours 30 minutes. It is filtered, the solid is then taken up with water and the mixture is filtered again. 5.9 g of the expected product are obtained.

Preparation 2.2

4-Cyano-1-hydrazinonaphthalene

A solution of 4.09 g of sodium nitrite in 30 ml of water is added to a solution, cooled to 0° C., of 8.35 g of 4-cyano-1-naphthylamine in 180 ml of 1N HCl. The mixture is left stirring for 1 hour 15 minutes at 0° C. It is cooled to −10° C., and a solution of 41.75 g of stannous chloride dihydrate in 42 ml of concentrated HCl is added slowly. The reaction mixture is stirred for 1 hour, allowing the temperature to rise to RT. It is filtered. The residue is suspended in water and 20 ml of concentrated NaOH are added. The expected product is obtained after filtration, rinses with water and then drying under vacuum, m=8.6 g.

Preparation 2.3

4-Hydrazino-1-naphthalenesulphonic Acid Hydrochloride 4 g of NaOH are added to a suspension of 22.33 g of 4-amino-1-naphthalenesulphonic acid in 125 ml of water. The mixture is cooled to 0° C. and 2 ml of concentrated NaOH are added, followed by 7.5 g of sodium nitrite and 125 g of ice to maintain the temperature at 0° C. The suspension thereby obtained is poured into 75 ml of concentrated HCl cooled beforehand to 0° C., and left stirring for 2 hours 15 minutes at this temperature. The reaction mixture is added slowly to a solution, cooled beforehand to −10° C., of 55 g of stannous chloride dihydrate in 50 ml of concentrated HCl and 25 ml of water. After one night, the expected product is obtained by filtration, rinsing with 1N HCl and with water, m=23.96 g.

Preparation 2.4

4-Hydrazino-1-naphthaleneacetic Acid Hydrochloride

A) 4-Amino-1-naphthaleneacetic Acid Hydrochloride

This compound is prepared according to the method described by Y. Ogata et al., J. Org. Chem., 1951, 16, 1588.

B) 4-Hydrazino-1-naphthaleneacetic Acid Hydrochloride 3.18 g of the compound obtained in the preceding step are mixed a −5° C. with 30 ml of concentrated HCl and 30 ml of AcOH. A solution of 1 g of sodium nitrite in 15 ml of water is added rapidly and the mixture is left stirring for 2 hours at a temperature of between −5° C. and +4° C. A solution of 14.2 g of stannous chloride dihydrate in 19 ml of concentrated HCl is then added, and the mixture is left stirring for 30 minutes at 0° C. The temperature is allowed to rise to RT and the reaction mixture is left stirring for 1 hour. It is filtered, and the crystals collected are stirred for 1 hour in MeCN. The expected product is obtained after filtration, m=2.4 g, m.p.=180° C.

Preparation 2.5

4-Hydrazino-1-naphthalenecarboxylic Acid Hydrochloride

A) 4-Amino-1-naphthalenecarboxylic Acid Methanesulphonate 2.8 ml of a 1.6M solution of n-butyllithium in hexane are added under an argon atmosphere to a solution, cooled to −15° C., of 5 g of 4-bromo-1-naphthylamine in 90 ml of ether, and the mixture is left stirring for 1 hour at −15° C. A solution of 5 g of 1,2-bis(chlorodimethylsilyl)ethane in 50 ml of ether is then added, the mixture is left stirring for 30 minutes at −10° C. and the temperature is allowed to rise to RT. The mixture is cooled to −5° C., 15 ml of a 1.6M solution of n-butyllithium in hexane are added and the mixture is left stirring for 1 hour at 0° C. A stream of carbon dioxide is then bubbled into the reaction mixture for 2 hours at a temperature of between 0° and 5° C. 2.86 ml of chlorotrimethylsilane are then added and the mixture is left stirring for 30 minutes. Water is then added, the mixture is extracted with AcOEt, the organic phase is dried over $Na_2SO_4$ and the solvent is evaporated off under vacuum. The residue is dissolved in acetone, 1.46 ml of methanesulphonic acid are added, and the precipitate formed is drained and washed with ether. 4 g of the expected product are obtained, m.p.=180° C. (dec.).

This compound is also obtained according to the procedure described below.

A') 4-Amino-1-naphthalenecarboxylic Acid

A mixture of 32 g of 4-cyano-1-naphthylamine in 400 ml of a 50% solution of KOH in water is heated to reflux overnight. After cooling, 800 ml of water are added to the reaction mixture and some insoluble matter is filtered off. The filtrate is cooled to +5° C. and acidified to pH 5 by adding concentrated HCl. The precipitate formed is drained and, after drying, 35 g of the expected product are obtained.

This compound is also obtained according to the two steps of the process described below.

A") 4-Nitro-1-naphthalenecarboxylic Acid

This compound is prepared according to J. Am. Chem. Soc., 1929, 51, 1831–1836, from 4-nitro-1,8-naphthalic anhydride.

B") 4-Amino-1-naphthalenecarboxylic Acid Hydrochloride

A mixture of 35 g of the compound prepared in step A", 1 liter of MeOH and 200 ml of DMF is hydrogenated in a Parr apparatus under a pressure of 8 bars and in the presence of Raney® nickel. After 4 hours the catalyst is filtered off and the filtrate is evaporated under vacuum. The residue is taken up in water, the mixture is left stirring overnight and the precipitate is drained. The precipitate is dissolved in a saturated solution of hydrochloric acid in MeOH, and ether is added until precipitation occurs. After draining and then drying, 21.4 g of the expected product are obtained.

B) 4-Hydrazino-1-naphthalenecarboxylic Acid Hydrochloride 2.4 g of 4-amino-1-naphthalenecarboxylic acid hydrochloride are mixed at 0° C. with 80 ml of concentrated HCl. A solution of 0.89 g of sodium nitrite in 19 ml of water is added and the mixture is left stirring for 2 hours at 2–3° C. It is cooled to −10° C., and a solution of 9.7 g of stannous chloride dihydrate in 90 ml of concentrated HCl is added slowly. The temperature is allowed to rise to RT and the mixture is kept stirring for 30 minutes. 200 ml of water are added, the mixture is left stirring for 30 minutes and the solid formed is drained. The solid is taken up in MeCN, drained, washed with ether and dried. 2.2 g of the expected product are obtained, m.p.=190° C.

This compound is also obtained according to the three steps of the process described below.

A''') N-ter-butoxycarbonyl-4-bromo-1-naphtylamine

A mixture of 5 g of 4-bromo-1-naphtylamine and 6.4 g of di-tert-butyldicarbonate in 120 ml of tertbutanol is heated to reflux for 20 hours. The reaction mixture thereby obtained is poured into 250 ml of water; the precipitate so formed is drained, washed with water, dissolved into DCM and the organic phase is dried over $Na_2SO_4$ and the solvent is evaporated off under vacuum. 6.9 g of the expected product are obtained; m.p.=134° C.

B''') 4-tert-butoxycarbonylaminonaphtalene-1-carboxylic Acid 21.3 ml of a solution of 1.6M n-butyllithium in hexane is added under nitrogen atmosphere to a solution of 5 g of the compound obtained in step A''') in 100 ml of ether, cooled to −10° C. The mixture is left stirring for 1 hour 30 minutes at 0° C. The reaction mixture is cooled to −10° C. and a stream of carbon dioxide is then bubbled into the reaction mixture for 15 minutes. Then 250 ml of water are added and after decantation the aqueous phase is washed with ether. The aqueous phase is then acidified to pH 6 by adding AcOH, extracted with DCM, the organic phase is dried over $Na_2SO_4$ and the solvent is evaporated off under vacuum. 2.7 g of the expected product are obtained, m.p.=214° C.

C''') Methanesulfonate of the 4-aminonaphtalene-1-carboxylic Acid

A solution of 15.8 ml of methanesulfonic acid in 50 ml of DCM is added dropwise at RT into a suspension of 7 g of the compound obtained in step B''') in 70 ml of DCM. After stirring at RT for 45 minutes, 150 ml of ether are added to the reaction mixture and the precipitate so formed is drained. After washing of the precipitate with ether and drying, 6.5 g of the expected product are obtained; m.p.=196° C. (decomposition).

Preparation 2.6

4-Hydrazino-1,8-naphthalimide Hydrochloride

A) 4-Sulpho-1,8-naphthalimide Potassium Salt

A mixture of 25 g of 4-sulpho-1,8-naphthalic anhydride potassium salt and 300 ml of 30% aqueous ammonia solution is left stirring for 2 hours at 60°–70° C. After one night at RT, the precipitate formed is drained and washed with water and then with EtOH. 21 g of the expected product are obtained, m.p.>300° C.

B) 4-Hydrazino-1,8-naphthalimide Hydrochloride

A mixture of 7 g of the compound obtained in the preceding step, 3.5 ml of hydrazine monohydrate and 100 ml of water is heated for 4 days to 80° C. After cooling, it is acidified to pH 1 by adding 1N HCl, and the precipitate formed is drained. 3.5 g of the expected product are obtained after trituration in an EtOH/ether mixture, followed by draining, m.p.=278° C.

Preparation 2.7

N-Amino-4-hydrazino-1,8-naphthalimide
(Compound 5)

A mixture of 25 g of 4-sulpho-1,8-naphthalic anhydride potassium salt and 50 ml of hydrazine monohydrate is heated to 120° C. for 1.5 days. After cooling, water is added to the reaction mixture, and the precipitate formed is drained and dried. 15.7 g of the expected product are obtained, m.p.=260° C.

PREPARATIONS OF THE ESTERS IIa, II'a AND II"a

Preparation 3.1

5-(2,6-Dimethoxyphenyl)-1-(4-nitro-1-naphthyl)-3-pyrazolecarboxylic Acid Methyl Ester (II'a: R'=$NO_2$; T=Me)

A mixture of 10 g of the compound obtained in Preparation 2.1, 13.5 g of compound obtained in Preparation 1 and 200 ml of AcOH is heated to reflux for 5 hours 30 minutes. After filtering off the insoluble matter, the filtrate is poured into 2 liters of a mixture of water and ice. The precipitate obtained is filtered off and stirred in 300 ml of iso ether. 14.8 g of the expected product are obtained after filtration, m.p.=180° C.

Preparation 3.2

1-(4-Cyano-1-naphthyl)-5-(2,6-dimethoxyphenyl)-3-pyrazolecarboxylic Acid Methyl Ester (IIa: R=CN, T=Me)

A mixture of 8.6 g of the compound obtained in Preparation 2.2, 13.5 g of compound obtained in Preparation 1 and 85 ml of AcOH is heated to reflux for 5 hours 15 minutes. After one night at RT, the reaction mixture is poured into a mixture of water and ice. The precipitate obtained is filtered off and washed with water. The product is chromatographed on silica, eluting with DCM and then DCM/AcOEt (98:2; v/v). 5.38 g of the expected product are obtained, m.p.=165° C.

Preparation 3.3

5-(2,6-Dimethoxyphenyl)-1-(4-sulpho-1-naphthyl)-3-pyrazolecarboxylic Acid Methyl Ester (II'a: R'= $SO_3H$, T=Me)

A mixture of 22.9 g of the compound obtained in Preparation 2.3, 21.65 g of compound obtained in Preparation 1 and 150 ml of AcOH is heated to reflux for 2 hours. After cooling, the reaction mixture is poured into a mixture of water and ice, and the precipitate obtained is filtered off. The filtrate is cooled and the pH is adjusted to 5–6 by adding concentrated NaOH. The precipitate obtained is filtered off and washed with water. 28.66 g of the expected product are obtained, m.p.=236° C.

Preparation 3.4

1-[4-(Carboxymethyl)-1-naphthyl]-5-(2,6-dimethoxyphenyl)- 3-pyrazolecarboxylic Acid Methyl Ester (IIa: R=—$CH_2COOH$; T=Me)

A mixture of 2.4 g of the compound obtained in Preparation 2.4, 2.8 g of the compound obtained in Preparation 1 and 50 ml of AcOH is heated for 2 hours 30 minutes to 60°–70° C. After cooling, water is added to the mixture and the viscous oil formed is separated. This oil is dissolved in EtOH and added slowly to the aqueous solution. The mixture is stirred for 1 hour and the precipitate obtained is filtered off. 2.8 g of the expected product are obtained, m.p.=200° C.

Preparation 3.5

5-(2,6-Dimethoxyphenyl)-1-[4-(ethanecarboxamido)-1-naphthyl]-3-pyrazolecarboxylic Acid Methyl Ester (IIa: R=NHCOEt; T=Me)

A mixture of 0.87 g of the compound obtained in Preparation 3.1, 0.3 g of 10% palladium on charcoal and 5 ml of propionic anhydride in 5 ml of DMF is hydrogenated at 80° C. at atmospheric pressure for 33 hours. 0.5 ml of pyridine is then added and the mixture is left stirring overnight at RT. It is filtered through Celite®, the filter is rinsed with MeOH and the filtrate is evaporated under vacuum. It is chromatographed on silica H, eluting with a toluene/AcOEt (70:30; v/v) mixture. 0.45 g of the expected product is obtained, m.p.=110° C.

Preparation 3.6

1-[4-(Acetylaminomethyl)-1-naphthyl]-5-(2,6-dimethoxyphenyl)- 3-pyrazolecarboxylic Acid Methyl Ester (IIa: R=—$CH_2NHCOMe$; T=Me)

A mixture of 2 g of the compound obtained in Preparation 3.2, 30 ml of acetic anhydride and 0.2 g of platinum oxide is hydrogenated at atmospheric pressure for 12 hours at 60° C. and then 8 hours at 100° C. After filteration through Celite® and washing with AcOEt, water is added to the filtrate. The latter is extracted with AcOEt, the organic phase is dried over sodium sulphate and the solvent is evaporated off under vacuum. The expected product is obtained after chromatography on silica H, eluting with a gradient of a DCM/AcOEt (98:2; v/v to 60:40; v/v) mixture. 0.9 g of the expected product is obtained.

NMR spectrum at 200 MHz in DMSO: 1.95 ppm: s: 3 H 3.5 ppm: bs: 6 H 3.9 ppm: s: 3 H 4.75 ppm: d: 2 H 6.55 ppm: d: 2 H 6.95 ppm: s: 1 H 7.15 to 8.25 ppm: u.c.: 7 H 8.5 ppm: t: 1 H.

Preparation 3.7

5-(2,6-Dimethoxyphenyl)-1-[4-(dimethylaminosulphonyl)- 1-naphthyl]-3-pyrazolecarboxylic Acid Methyl Ester (IIa: R=—$SO_2N(Me)_2$; T=Me)

A) 1-[4-(Chlorosulphonyl)-1-naphthyl]-5-(2,6 -dimethoxyphenyl)-3-pyrazolecarboxylic Acid Methyl Ester (II'a: R'=—$SO_2Cl$; T=Me)

A mixture of 5 g of the compound obtained in Preparation 3.3 and 3.21 g of phosphorus pentachloride in 100 ml of DCM is stirred at RT for 5 hours. The mixture is evaporated to dryness under vacuum and the residue is heated to 110° C. for 1 hour. It is left overnight at RT. The residue is taken up several times with toluene, DCM and 1,2-dichloroethane, followed each time by an evaporation under vacuum. 5.9 g of the expected product are obtained, which product is used in the next step without further treatment.

B) 5-(2,6-Dimethoxyphenyl)-1-[4-(dimethylaminosulphonyl)- 1-naphthyl]-3-pyrazolecarboxylic Acid Methyl Ester (IIa: R=—$SO_2N(Me)_2$, T=Me)

Gaseous dimethylamine is introduced for 45 minutes into a solution of 5.9 g of the compound obtained in the preceding step in 100 ml of DCM to which 1,2-dichloroethane and DMF are added until the compound has dissolved. The mixture is then left stirring at RT for 3 hours 30 minutes.

After filtering off some insoluble matter, the filtrate is evaporated under vacuum. The residue is extracted with AcOEt, the organic phase is washed with water and dried over sodium sulphate and the solvent is evaporated off under vacuum. 2.67 g of the expected product are obtained.

NMR spectrum at 200 MHz in DMSO: 2.65 ppm: s: 6 H 3.35 ppm: bs: 6 H 6.45 ppm: d: 2 H 6.95 ppm: s: 1 H 7.15 ppm: t: 1 H 7.3 to 8.8 ppm: u.c.: 6 H.

Preparation 3.8

5-(2,6-Dimethoxyphenyl)-1-[4-{N-methyl-N-[3-(N',N'-dimethylamino)propyl]aminosulphonyl}-1-naphthyl]-3-pyrazolecarboxylic Acid Methyl Ester (IIa: R=—SO$_2$N(Me)(CH$_2$)$_3$N(Me)$_2$; T=Me)

2.34 g of the compound obtained in step A of Preparation 3.7 are dissolved under reflux in 50 ml of toluene, the mixture is cooled to RT and 1.4 ml of N,N,N'-trimethyl-1,3-propanediamine are added. The mixture is then stirred at RT for 2 hours 45 minutes and 0.7 ml of N,N,N'-trimethyl-1,3-propanediamine is added. After 45 minutes of stirring at RT, some insoluble matter is filtered off and the filtrate is evaporated under vacuum. The residue is extracted with AcOEt, the organic phase is washed with water and dried over sodium sulphate and the solvent is evaporated off under vacuum. The product is chromatographed on silica, eluting with a DCM/MeOH (100:6; v/v) mixture. 0.82 g of the expected product is obtained, m.p.=87° C.

Preparation 3.9

1-[4-(Carbamoylmethyl)-1-naphthyl]-5-(2,6-dimethoxyphenyl)-3-pyrazolecarboxylic Acid Methyl Ester (IIa: R=—CH$_2$CONH$_2$; T=Me)

A mixture of 1.4 g of the compound obtained in Preparation 3.4 and 3 ml of thionyl chloride in 30 ml of DCM is heated to 40° C. for 3 hours; it is then evaporated to dryness under vacuum. A solution of the acid chloride prepared above in THF is added to 20 ml of a 0.4N solution of ammonia in THF. The reaction mixture is left stirring overnight at RT and evaporated under vacuum. The residue is taken up in water and the precipitate formed is filtered off. The expected product is obtained, which product is used in Preparation 4.8 without further treatment.

Preparation 3.10

1-(4-Amino-1-naphthyl)-5-(2,6-dimethoxyphenyl)-3-pyrazolecarboxylic Acid Methyl Ester (II'a: R'=NH$_2$l; T=Me)

A mixture of 7.5 g of the compound prepared in Preparation 3.1 and 0.75 g of Raney® nickel in 200 ml of MeOH is hydrogenated at RT for 6 days at atmospheric pressure. The reaction mixture is filtered through Celite®, the filter is washed with 100 ml of DMF and the solvents are evaporated off under vacuum. 0.7 g of the expected product is obtained after crystallization in iso ether, m.p.=246° C.

Preparation 3.11

5-(2,6-Dimethoxyphenyl)-1-(4-hydroxy-1-naphthyl)-3-pyrazolecarboxylic Acid Methyl Ester (II'a: R'=OH; T=Me)

A solution of 0.475 g of sodium nitrite in 25 ml of water is added to a mixture, cooled to 0° C., of 2.5 g of the compound prepared in Preparation 3.10 in 50 ml of 35% H$_2$SO$_4$. The mixture is left stirring for 1 hour 30 minutes at 3° C., and 1.3 g of diazonium salt are obtained after filtering off the crystals formed, followed by drying. The diazonium salt thus prepared is added to a solution of 130 g of copper nitrate in 800 ml of water, and the mixture is left stirring for 30 minutes. 1 g of iron sulphate is then added and the mixture is left stirring for 2 hours. After filtration of the reaction mixture, the residue is taken up in MeOH and left stirring in the presence of animal charcoal. The mixture is filtered through Celite® and the filtrate is evaporated under vacuum. 0.69 g of the expected product is obtained after crystallization in EtOH, m.p.=240° C.

Preparation 3.12

5-(2,6-Dimethoxyphenyl)-1-{4-[3-(N,N-dimethylamino)propoxy]-1-naphthyl}-3-pyrazolecarboxylic Acid Methyl Ester (IIa: R=—O(CH$_2$)$_3$N(Me)$_2$; T=Me)

0.44 g of the compound prepared in Preparation 3.11, 0.19 ml of a 50% solution of caesium hydroxide in water and 1 ml of MeOH are mixed, and the mixture is then evaporated to dryness. The residue is taken up in 5 ml of DMF, and 0.48 g of 3-chloro-N,N-dimethylpropylamine hydrochloride is added, followed by 1.44 g of potassium carbonate. The mixture is heated for 3 hours to 60°. After cooling, water is added, the mixture is extracted with AcOEt, the organic phase is dried over sodium sulphate and the solvent is evaporated off under vacuum. The product is chromatographed on silica, eluting with a DCM/MeOH/NH$_4$OH (100:5:0.5; v/v/v) mixture. 0.25 g of the expected product is obtained.

NMR spectrum at 200 MHz in DMSO: 1.9 ppm: qt: 2 H 2.1 ppm: s: 6 H 2.4 ppm: mt: 2 H 3.35 ppm: s: 6 H 3.7 ppm: s: 3 H 4.1 ppm: t: 2 H 6.35 ppm: d: 2 H 6.8 ppm: s: 1 H 6.95 to 8.1 ppm: u.c.: 7 H.

Preparation 3.13

1-[4-(Carbamoylmethoxy)-1-naphthyl]-5-(2,6-dimethoxyphenyl)- 3-pyrazolecarboxylic Acid Methyl Ester (IIa: R=—OCH$_2$CONH$_2$, T=Me)

0.39 g of the compound prepared in Preparation 3.11, 0.17 ml of a 50% solution of caesium hydroxide in water and 1 ml of MeOH are mixed, and the mixture is then evaporated to dryness. The residue is taken up in 5 ml of DMF, and 0.193 g of 2-bromoacetamide is added. The mixture is heated for 2 hours to 60°. After cooling, water is added, the mixture is extracted with AcOEt, the organic phase is dried over sodium sulphate and the solvent is evaporated off under vacuum. 0.28 g of the expected product is obtained, which product is used in Preparation 4.10 without further treatment.

Preparation 3.14

1-(4-Carboxy-1-naphthyl)-5-(2,6-dimethoxyphenyl)-
3-pyrazolecarboxylic Acid Methyl Ester (II'a: R'=—COOH; T=Me)

A mixture of 2.2 g of the compound obtained in Preparation 2.5, 2.65 g of the compound obtained in Preparation 1 and 200 ml of AcOH is heated to reflux for 3 hours. After cooling, 700 ml of water are added and the precipitate formed is drained. The precipitate is taken up in 1,4-dioxane and the solvent is evaporated off under vacuum. After drying, 2.75 g of the expected product are obtained, m.p.= 240° C.

Preparation 3.15

5-(2,6-Dimethoxyphenyl)-1-[4-{N-[3-(N',N'-
dimethylamino)propyl]carbamoyl}-1-naphthyl]-
3-pyrazolecarboxylic Acid Methyl Ester (IIa: R=—CONH(CH$_2$)$_3$N(Me)$_2$; T=Me)

A mixture of 0.5 g of the compound obtained in Preparation 3.14 and 5 ml of thionyl chloride are left stirring for 2 hours, and the mixture is then concentrated under vacuum. The acid chloride thereby obtained is taken up in 5 ml of DCM, this solution is then added dropwise to a solution of 0.165 ml of N,N-dimethyl- 1,3-propanediamine and 0.172 ml of triethylamine in 10 ml of DCM, and the mixture is left stirring overnight at RT. Water is added to the reaction mixture, the organic phase is separated after settling has taken place and dried over Na$_2$SO$_4$ and the solvent is evaporated off under vacuum. 0.52 g of the expected product is obtained.

NMR spectrum at 200 MHz in DMSO: 1.8 to 2.0 ppm: mt: 2 H 2.8 ppm: s: 6 H 3.05 to 3.40 ppm: 2 t: 4 H 3.4 ppm: s: 6 H 6.5 ppm: d: 2 H 7.0 ppm: s: 1 H 7.1 to 7.2 ppm: t: 1 H 7.4 ppm: d: 1 H 7.45 to 7.70 ppm: u.c.: 4 H 8.20 ppm: mt: 1 H.

Preparation 3.16

5-(2,6-Dimethoxyphenyl)-1-[4-{N-[2-(N',N'-
dimethylamino)ethyl]carbamoyl}-1-naphthyl]-3-
pyrazolecarboxylic Acid Methyl Ester (IIa: R=—CONH(CH$_2$)$_2$N(Me)$_2$; T=Me)

This compound is prepared according to the procedure described in Preparation 3.15, from 0.5 g of the compound obtained in Preparation 3.14, 5 ml of thionyl chloride and then 0.155 ml of N,N-dimethylethylenediamine and 0.196 ml of triethylamine. 0.6 g of the expected product is obtained.

NMR spectrum at 200 MHz in DMSO: 2.8 ppm: s: 6 H 3.2 to 3.8 ppm: u.c.: 10 H 3.9 ppm: s: 3 H 6.8 ppm: d: 2 H 7.0 ppm: s: 1 H 7.2 ppm: t: 1 H 7.4 ppm: d: 1 H 7.45 to 7.70 ppm: u.c.: 3 H 7.8 ppm: d: 1 H 8.3 ppm: u.c.: 1 H 10.2 ppm: bs: 1 H.

Preparation 3.17

1-{4-[N-(Cyanomethyl)carbamoyl]-1-naphthyl}-5-(
2,6-dimethoxyphenyl)-3-pyrazolecarboxylic Acid
Methyl Ester (IIa: R=—CONHCH$_2$CN; T=Me)

This compound is prepared according to the procedure described in Preparation 3.15, from 1.22 g of the compound obtained in Preparation 3.14, 12 ml of thionyl chloride and then 0.269 g of aminoacetonitrile hydrochloride and 0.8 ml of triethylamine. 0.77 g of the expected product is obtained after crystallization in EtOH, m.p.=138°–140° C.

Preparation 3.18

1-{4-[N-(2–Cyanoethyl)-N-methylcarbamoyl]-1-
naphthyl}- 5-(2,6-dimethoxyphenyl)-3-pyrazole-
carboxylic Acid Methyl Ester (IIa: R=—CON(Me)CH$_2$CH$_2$CN; T=Me)

This compound is prepared according to the procedure described in Preparation 3.15, from 10 g of the compound obtained in Preparation 3.14, 15 ml of thionyl chloride and then 2.4 ml of 3-methylaminopropionitrile and 3.3 ml of triethylamine. 12 g of the expected product are obtained.

NMR spectrum at 200 MHz in DMSO: 2.6 ppm: s: 3 H 2.8 ppm: t: 2 H 3.3 ppm: s: 6 H 3.9 ppm: u.c.: 5 H 6.4 ppm: d: 2 H 6.9 ppm: s: 1 H 7.1 ppm: t: 1 H 7.2 to 7.8 ppm: u.c.: 6 H.

Preparation 3.19

5-(2,6-Dimethoxyphenyl)-1-[4-(N-methylcarbamoyl)-
1-naphthyl]-3-pyrazolecarboxylic Acid
Methyl Ester (IIa: R=—CONHMe; T=Me)

A mixture of 4 g of the compound obtained in Preparation 3.14 and 20 ml of thionyl chloride in 20 ml of DCM is heated to 40° C. for 2 hours and is then concentrated under vacuum. The acid chloride thereby obtained is taken up in 40 ml of DCM, and the mixture is added dropwise to a solution, cooled beforehand to 5° C., of 4 ml of a 40% aqueous solution of methylamine in 80 ml of MeOH. The mixture is left stirring overnight at RT and concentrated under vacuum, the residue is taken up with water and the precipitate formed is drained. After drying, the expected product is obtained, which product is used in Preparation 4.15 without further treatment.

Preparation 3.20

5-(2,6-Dimethoxyphenyl)-1-[4-(6-acetamidohex-
anoylamino)- 1-naphthyl]-3-pyrazolecarboxylic
Acid Methyl Ester (IIa: R=—NHCO(CH$_2$)$_5$NHCOMe; T=Me)

A) 6-Acetamidohexanoyl Chloride

A mixture of 0.37 g of 6-acetamidohexanoic acid and 2.5 ml of thionyl chloride is left stirring for 24 hours at RT. It is concentrated under vacuum, and the acid chloride thereby obtained is used in the next step without further treatment.

B) 5-(2,6-Dimethoxyphenyl)-1-[4-(6-acetamidohexanoy-
lamino)- 1-naphthyl]-3-pyrazolecarboxylic Acid Methyl Ester A mixture of 0.5 g of the compound obtained in Preparation 3.10 and 0.5 ml of bis(trimethylsilyl)acetamide in 5 ml of MeCN is left stirring overnight at RT. A solution of the compound obtained in the preceding step in 5 ml of MeCN is then added, followed by 2 ml of triethylamine. The mixture is left stirring for two days at RT, 5 ml of MeOH and 5 ml of water are added, and the mixture is left stirring for 15 minutes and concentrated under vacuum. The residue is extracted with 50 ml of DCM, the organic phase is washed with water and with 1N HCl solution and dried over $Na_2SO_4$ and the solvent is concentrated under vacuum. 0.7 g of the expected product is obtained, which product is used in Preparation 4.16 without further treatment.

Preparation 3.21

5-(2,6-Dimethoxyphenyl)-1-[4-{N-methyl-N-[3-(N',N'-dimethylamino)propyl]carbamoyl}-1-naphthyl]-3-pyrazolecarboxylic Acid Methyl Ester (IIa: R=—CON(Me)(CH$_2$)$_3$N(Me)$_2$; T=Me)

This compound is prepared according to the procedure described in Preparation 3.15, from 0.5 g of the compound obtained in Preparation 3.14, 5 ml of thionyl chloride and then 0.120 ml of N,N,N'-trimethyl- 1,3-propanediamine and 0.170 ml of triethylamine. 0.43 g of the expected product is obtained.

Preparation 3.22

5-(2,6-Dimethoxyphenyl)-1-[4-{N-methyl-N-[2-(N',N'-dimethylamino)ethyl]carbamoyl}-1-naphthyl]-3-pyrazolecarboxylic Acid Methyl Ester (IIa: R=—CON(Me)(CH$_2$)$_2$N(Me)$_2$; T=Me)

This compound is prepared according to the procedure described in Preparation 3.15 from 0.5 g of the compound obtained in Preparation 3.14, 5 ml of thionyl chloride and then 0.179 ml of N,N,N'-trimethylethylenediamine and 0.2 ml of triethylamine. 0.4 g of the expected product is obtained.

Preparation 3.23

5-(2,6-Dimethoxyphenyl)-1-[1,3(2H)-dioxo-1H-benz[de]isoquinol-6-yl]-3-pyrazolecarboxylic Acid Methyl Ester

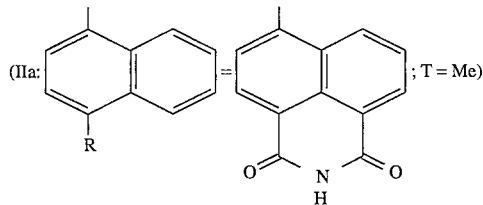

(IIa: ; T = Me)

A mixture of 2 g of the compound obtained in Preparation 2.6, 2.4 g of the compound obtained in Preparation 1 and 50 ml of AcOH is heated to reflux for 3 hours. After cooling, water is added and the precipitate formed is drained. The precipitate is chromatographed on silica, eluting with a DCM/MeOH (100:2; v/v) mixture. 2.4 g of the expected product are obtained, m.p.=138° C. (dec.).

Preparation 3.24

5-(2,6-Dimethoxyphenyl)-1-[2-amino-1,3(2H)-dioxo-1H-benz[de]isoquinol-6-yl]-3-pyrazolecarboxylic Acid Methyl Ester (II"a: T=Me)

A mixture of 3 g of the compound obtained in Preparation 2.7, 3.6 g of the compound obtained in Preparation 1 and 70 ml of AcOH is heated to 70° C. for 2 hours. It is concentrated under vacuum, the residue is taken up with water and the precipitate formed is drained and dried. The precipitate is chromatographed on silica, eluting with a DCM/AcOH (100:5; v/v) mixture. 3.3 g of the expected product are obtained, which product is used in Preparation 4.20 without further treatment.

PREPARATIONS OF THE ACIDS II, II' and II"

Preparation 4.1

5-(2,6-Dimethoxyphenyl)-1-(4-nitro-1-naphthyl)-3-pyrazolecarboxylic Acid (II': R'=—NO$_2$; T=Me)

A mixture of 14.8 g of the ester obtained in Preparation 3.1, 5.8 g of KOH, 12 ml of water and 50 ml of MeOH is heated for 1 hour 30 minutes to 40° C. The solvents are evaporated off under vacuum and the residue is taken up with 250 ml of water. The mixture is acidified at 10° C. to pH 1 by adding 1N HCl. The precipitate formed is filtered off and washed twice with water. 14.64 g of the expected product are obtained after recrystallization in iso ether, m.p.=55° C.

Preparation 4.2

5-(2,6-Dimethoxyphenyl)-1-[4-(ethanecarboxamido)-1-naphthyl]-3-pyrazolecarboxylic Acid (II: R=—NHCOEt; T=Me)

A mixture of 0.35 g of the compound obtained in Preparation 3.5, and 0.07 g of lithium hydroxide monohydrate in 2 ml of EtOH is stirred at RT for 4 hours 30 minutes. It is evaporated under vacuum, the residue is taken up in 5 ml of 1N HCl and the mixture is left stirring for 1 hour. 0.27 g of the expected product is obtained after filtration and washes with water, m.p.=168° C.

Preparation 4.3

1-(4-Cyano-1-naphthyl)-5-(2,6-dimethoxyphenyl)-3-pyrazolecarboxylic Acid (II: R=—CN; T=Me)

A mixture of 4.88 g of the ester obtained in Preparation 3.2 and 1.2 ml of concentrated NaOH in 500 ml of MeOH is stirred overnight at RT. The reaction mixture is heated for 3 hours to 40° C. and concentrated under vacuum to one half the volume. 1.2 ml of concentrated NaOH are added and the mixture is heated for 6 hours to 40° C. After 48 hours at RT, the reaction mixture is partially concentrated and poured into a mixture of water and ice. The resulting mixture is extracted with ether, the aqueous phase is acidified to pH 4 by adding 1.2N HCl and extracted with AcOEt, the organic phase is dried over sodium sulphate and the solvent is evaporated off under vacuum. 4.6 g of expected product are obtained, m.p.=216° C.

Preparation 4.4

1-(4-Carbamoyl-1-naphthyl)-5-(2,6-dimethoxyphenyl)- 3-pyrazolecarboxylic Acid (II: R=—CONH$_2$; T=Me)

A mixture of 1.48 g of the compound obtained in Preparation 3.2, 3 ml of 6N NaOH and 3 ml of hydrogen peroxide (33% aqueous solution) in 15 ml of 95% EtOH is heated to reflux for 1 hour 20 minutes. It is then stirred at RT overnight. The precipitate obtained is filtered off and rinsed with 95% EtOH. To a suspension in water of the solid collected, concentrated HCl is added to pH 1. 0.92 g of the expected product is obtained after filtration, washes with water and drying, m.p.=305° C.

Preparation 4.5

1-[4-(Acetylaminomethyl)-1-naphthyl]-5-(2,6-dimethoxyphenyl)- 3-pyrazolecarboxylic Acid (II: R=—$CH_2NHCOMe$; T=Me)

A mixture of 0.8 g of the compound obtained in Preparation 3.6 and 0.1 g of lithium hydroxide monohydrate in 12 ml of MeOH and 1.5 ml of water is stirred at RT for days. The reaction mixture is poured into a mixture of water and ice and the resulting mixture is washed with ether. The aqueous phase is acidified to pH 2 by adding 1.2N HCl. 0.58 g of the expected product is obtained after filtering off the precipitate formed, washing with water and drying under vacuum over $P_2O_5$, m.p.=252° C.

Preparation 4.6

5-(2,6-Dimethoxyphenyl)-1-[4-(dimethylamino-sulphonyl)- 1-naphthyl]-3-pyrazolecarboxylic Acid (II: R=—$SO_2N(Me)_2$; T=Me)

A solution of 0.6 g of KOH in 0.5 ml of water is added at RT to a solution of 2.15 g of the compound obtained in Preparation 3.7 in 15 ml of dioxane. The reaction mixture is left stirring at RT for 1 hour and then left overnight. The said mixture is partially concentrated under vacuum and left stirring at RT for 4 hours. It is poured into a mixture of water and ice and the resulting mixture is washed with ether. The aqueous phase is acidified to pH 4–5 by adding 1.2N HCl. 2 g of the expected product are obtained after filtering off the precipitate formed, washing with water and drying under vacuum over $P_2O_5$, m.p.=209° C.

Preparation 4.7

5-(2,6-Dimethoxyphenyl)-1-[4-{N-methyl-N-[3-(N',N'-dimethylamino)propyl]aminosulphonyl}- 1-naphthyl]- 3-pyrazolecarboxylic Acid (II: R=—$SO_2N(Me)(CH_2)_3N(Me)_2$; T=Me)

A solution of 0.2 g of KOH in 0.5 ml of water is added at RT to a solution of 0.82 g of the compound obtained in Preparation 3.8 in 16 ml of dioxane. The mixture is left stirring at RT for 1 day and then poured into a mixture of water and ice. The resulting mixture is washed with ether and the aqueous phase is acidified to pH 1 by adding 1N HCl. The mixture is then extracted with DCM, the organic phase is dried over sodium sulphate and the solvent is evaporated off under vacuum. 0.68 g of the expected product is obtained after crystallization in ether, m.p.=176° C.

Preparation 4.8

1-[4-(Carbamoylmethyl)-1-naphthyl]-5-(2,6-dimethoxyphenyl)- 3-pyrazolecarboxylic Acid (II: R=—$CH_2CONH_2$; T=Me)

A mixture of the compound obtained in Preparation 3.9 and 0.35 g of KOH in 10 ml of 95% EtOH is heated to reflux for 2 hours. The reaction mixture is evaporated under vacuum and the residue is taken up with 1N HCl solution. 1.3 g of the expected product are obtained after filtering off the precipitate formed and then drying, m.p.= 262° C.

Preparation 4.9

5-(2,6-Dimethoxyphenyl)-1-{4-[3-(N,N-dimethylamino)propoxy]-1-naphthyl}-3-pyrazolecarboxylic Acid (II: R=—$O(CH_2)_3N(Me)_2$; T=Me)

A mixture of 0.25 g of the compound obtained in Preparation 3.12 and 0.025 g of lithium hydroxide monohydrate in 3 ml of MeOH and 0.4 ml of water is heated to 60° C. for 2 hours. The aqueous medium is evaporated under vacuum and neutralized to pH 7 by adding 1N HCl. 0.19 g of the expected product is obtained after filtering off the precipitate formed and then drying, and it is used in Example 16 without further treatment.

Preparation 4.10

1-[4-(Carbamoylmethoxy)-1-naphthyl]-5-(2,6-dimethoxyphenyl)- 3-pyrazolecarboxylic Acid (II: R=—$OCH_2CONH_2$; T=Me)

A mixture of 0.28 g of the compound obtained in Preparation 3.13 and 0.029 g of lithium hydroxide monohydrate in 3 ml of MeOH and 3 ml of water is heated to 60° C. for 4 hours. The mixture is evaporated under vacuum, water is added and the resulting mixture is acidified to pH 2 with N HCl. 0.31 g of the expected product is obtained after filtering off the precipitate formed and then drying, m.p.=224° C.

Preparation 4.11

5-(2,6-dimethoxyphenyl)-1-[4-{N-[3-(N',N'-dimethylamino)propyl]carbamoyl}-1-naphthyl]-3-pyrazolecarboxylic Acid (II: R=—$CONH(CH_2)_3N(Me)_2$; T=Me)

A mixture of 0.5 g of the compound obtained in Preparation 3.15 and 0.058 g of lithium hydroxide monohydrate in 15 ml of MeOH and 5 ml of water is heated to reflux for 2 hours. 1N HCl solution is added to pH 6 and the mixture is concentrated under vacuum. The residue is taken up with saturated NaCl solution, DCM is added and the solid formed is drained. This solid is taken up in EtOH, some insoluble matter is filtered off and the filtrate is evaporated under vacuum. 0.41 g of the expected product is obtained.

NMR spectrum at 200 MHz in DMSO: 1.5 to 1.7 ppm: qt: 2 H 2.2 ppm: s: 6 H 2.4 ppm: u.c.: 2 H 3.2 ppm: u.c.: 2 H 3.3 ppm: s: 6 H 6.4 ppm: d: 2 H 6.7 ppm: s: 1 H 7.1 ppm: t: 1 H 7.2 ppm: d: 1 H 7.3 to 7.5 ppm: u.c.: 4 H 8.0 ppm: u.c.: 1 H 8.6 ppm: t: 1 H.

Preparation 4.12

5-(2,6-Dimethoxyphenyl)-1-[4-{N-[2-(N',N'-dimethylamino)ethyl]carbamoyl}-1-naphthyl]-3-pyrazolecarboxylic Acid (II: R=—$CONH(CH_2)_2N(Me)_2$; T=Me)

A mixture of 0.6 g of the compound obtained in Preparation 3.16 and 0.088 g of lithium hydroxide monohydrate in 10 ml of MeOH and 10 ml of water is heated to 70° C. for 2 hours. The mixture is concentrated under vacuum, the residue is taken up with saturated NaCl solution, 1N HCl solution is added to pH 6.5, the mixture is extracted with DCM, the organic phase is dried over Na$_2$SO$_4$ and the solvent is evaporated off under vacuum. 0.44 g of the expected product is obtained, which product is used in Example 20 without further treatment.

Preparation 4.13

1-{4-[N-(Cyanomethyl)carbamoyl]-1-naphthyl}-5-(2,6-dimethoxyphenyl)-3-pyrazolecarboxylic Acid (II: R=—CONHCH$_2$CN; T=Me)

A mixture of 0.77 g of the compound obtained in Preparation 3.17 and 0.118 g of lithium hydroxide monohydrate in 15 ml of MeOH and 10 ml of water is heated to reflux for 1 hour 30 minutes, and is then concentrated under vacuum. The residue is taken up with saturated NaCl solution, the mixture is extracted with DCM, the organic phase is dried over Na$_2$SO$_4$ and the solvent is evaporated off under vacuum. 0.55 g of the expected product is obtained.

NMR spectrum at 200 MHz in DMSO: 3.4 ppm: s: 6 H 3.8 ppm: s: 2 H 6.4 ppm: d: 2 H 6.8 ppm: s: 1 H 7.1 ppm: t: 1 H 7.3 ppm: d: 1 H 7.4 to 7.6 ppm: u.c.: 4 H 8.2 ppm: u.c.: 1 H 8.8 ppm: u.c.: 1 H.

Preparation 4.14

1-{4-[N-(2–Cyanoethyl)-N-methylcarbamoyl]-1-naphthyl}-5-(2,6-dimethoxyphenyl)-3-pyrazolecarboxylic Acid (II: R=—CON(Me)CH$_2$CH$_2$CN; T=Me)

A mixture of 8 g of the compound obtained in Preparation 3.18 and 0.77 g of lithium hydroxide monohydrate in 100 ml of MeOH and 100 ml of water is left stirring overnight at RT. The reaction mixture is diluted by adding water, 1N HCl solution is then added to pH 2 and the precipitate formed is drained. After drying, 7.36 g of the expected product are obtained, m.p.=145° C.

Preparation 4.15

5-(2,6-Dimethoxyphenyl)-1-[4-(N-methylcarbamoyl)-1-naphthyl]-3-pyrazolecarboxylic Acid (II: R=—CONHMe; T=Me)

A mixture of the compound obtained in Preparation 3.19 and 0.69 g of lithium hydroxide monohydrate in 50 ml of MeOH and 50 ml of water is heated to 50° C. for 3 hours. 10% HCl solution is added to pH 2 and the precipitate formed is drained. After drying, the compound is recrystallized in MeOH and 3.3 g of the expected product are obtained, m.p.>260° C.

NMR spectrum at 200 MHz in DMSO: 2.8 ppm: s: 3 H 3.4 ppm: s: 6 H 6.4 ppm: d: 2 H 6.8 ppm: s: 1 H 7.1 ppm: t: 1 H 7.35 to 8.20 ppm: u.c.: 6 H 8.45 ppm: qr: 1 H Preparation 4.16

5-(2,6-Dimethoxyphenyl)-1-[4-(6-acetamidohexanoylamino)- 1-naphthyl]-3-pyrazolecarboxylic Acid (II: R=—NHCO(CH$_2$)$_5$NHCOMe; T=Me)

A mixture of 0.7 g of the compound obtained in Preparation 3.20 and 0.18 g of lithium hydroxide monohydrate in 5 ml of 1,4-dioxane and 1 ml of water is left stirring overnight at RT. The mixture is concentrated under vacuum, the residue is taken up in 10 ml of MeOH and 5 ml of water and the resulting mixture is heated to 45° C. for 2 hours in an ultrasonic bath. It is concentrated under vacuum, the residue is taken up in 20 ml of water, the mixture is washed with 30 ml of ether, the aqueous phase is acidified to pH 1 by adding concentrated H$_2$SO$_4$ and extracted twice with 500 ml of AcOEt, and the organic phase is dried over Na$_2$SO$_4$ and evaporated under vacuum. 0.4 g of the expected product is obtained, m.p.=140° C.

Preparation. 4.17

5-(2,6-Dimethoxyphenyl)-1-[4-{N-methyl-N-[3-(N',N'-dimethylamino)propyl]carbamoyl}-1-naphthyl]-3-pyrazolecarboxylic Acid (II: R=—CON(Me)(CH$_2$)$_3$N(Me)$_2$; T=Me)

A mixture of 0.41 g of the compound obtained in Preparation 3.21 and 0.043 g of lithium hydroxide monohydrate in 15 ml of MeOH and 5 ml of water is heated at reflux for 2 hours. The mixture is concentrated under vacuum, the residue is taken up with saturated NaCl solution, 1N HCl solution is added to pH 6, the mixture is extracted with DCM, the organic phase is dried over Na$_2$SO$_4$ and the solvent is evaporated off under vacuum. 0.33 g of the expected product is obtained.

Preparation 4.18

5-(2,6-Dimethoxyphenyl)-1-[4-{N-methyl-N-[2-(N',N'-dimethylamino)ethyl]carbamoyl}-1-naphthyl]-3-pyrazolecarboxylic Acid (II: R=—CON(Me)(CH$_2$)$_2$N(Me)$_2$; T=Me)

A mixture of 0.38 g of the compound obtained in Preparation 3.22 and 0.052 g of lithium hydroxide monohydrate in 5 ml of MeOH and 5 ml of water is heated to reflux for 2 hours. The mixture is concentrated under vacuum, the residue is taken up with saturated NaCl solution, 1N HCl solution is added to pH 6.5, the mixture is extracted with DCM, the organic phase is dried over Na$_2$SO$_4$ and the solvent is evaporated off under vacuum. 0.32 g of the expected product is obtained.

Preparation 4.19

5-(2,6-Dimethoxyphenyl)-1-[1,3(2H)-dioxo-1H-benz[de]isoquinol-6-yl]-3-pyrazolecarboxylic Acid

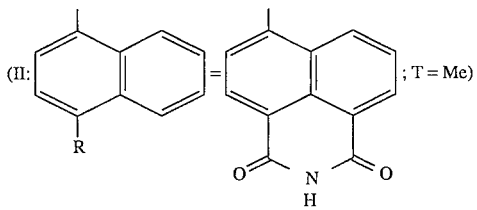

A mixture of 2.4 g of the compound obtained in Preparation 3.23, 0.375 g of lithium hydroxide monohydrate, 10 ml of MeOH and 10 ml of water is left stirring overnight at RT, and is then heated for 2 hours to 60° C. After cooling, the mixture is acidified to pH 2 by adding 1N HCl, and the precipitate formed is drained. 2.3 g of the expected product are obtained, m.p.=190° C. (dec.).

Preparation 4.20

5-(2,6-Dimethoxyphenyl)-1-[2-amino-1,3(2H)-dioxo-1H-benz[de]isoquinol-6-yl]-3-pyrazolecarboxylic Acid Hydrochloride (II": T=Me)

A mixture of 3.3 g of the compound obtained in Preparation 3.24, 0.7 g of lithium hydroxide monohydrate, 15 ml of MeOH and 15 ml of water is left stirring overnight at RT. The reaction mixture is acidified to pH 2 by adding 1N HCl, and the precipitate formed is drained and dried. 2.76 g of the expected product are obtained, m.p.=180° C.

Preparation 4.21

5-(2,6-Dimethoxyphenyl)-1-[2-acetamido-1,3(2H)-dioxo-1H-benz[de]isoquinol-6-yl]-3-pyrazolecarboxylic Acid

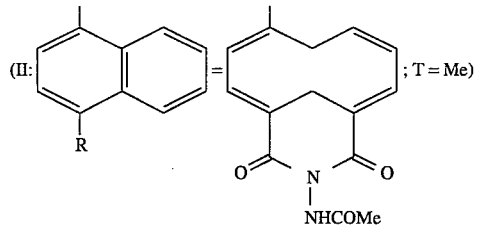

A mixture of 2.26 g of the compound obtained in Preparation 4.20, 1.13 ml of acetic anhydride, 0.407 g of sodium bicarbonate and 75 ml of AcOH is left stirring overnight at RT. Water is added to the reaction mixture, and the precipitate formed is drained and dried. 1.9 g of the expected product are obtained, m.p.=250° C.

PREPARATION OF A COMPOUND III (S)-Cyclohexylglycine Methyl Ester Hydrochloride A) (S)-N-tert-Butoxycarbonylcyclohexylglycine A mixture of 10.7 g of (S)-N-tert-butoxycarbonylphenylglycine and 2 g of 5% rhodium on alumina in 100 ml of MeOH is hydrogenated at RT for 4 days at 70 bars pressure. The catalyst is filtered off on Celite® and the filtrate is evaporated under vacuum. 11.1 g of the expected product are obtained. $\alpha_D^{20°}$=+3.5 [c=1; DMF]

B) (S)-Cyclohexylglycine Trifluoroacetate 50 ml of TFA are added rapidly to a solution, cooled to 0° C., of 11 g of the compound obtained in the preceding step in 50 ml of DCM. The mixture is left stirring for 1 hour at RT and evaporated under vacuum. The residue is taken up in iso ether and the precipitate formed is filtered off. 7.6 g of the expected product are obtained, m.p.>260° C. $\alpha_D^{20°}$=+19.2 [c=2; HCl 5N]

C) (S)-Cyclohexylglycine Methyl Ester Hydrochloride 10 ml of thionyl chloride are added dropwise to a solution, cooled to −10° C., of 1.2 g of the compound obtained in the preceding step in 200 ml of MeOH. The mixture is allowed to return to RT and is heated to reflux for 2 hours. It is evaporated to dryness, the residue is taken up in toluene and the mixture is then evaporated under vacuum; this operation is repeated twice. 1 g of the expected product is obtained, m.p.>260° C.

NMR spectrum at 200 MHz in DMSO: 0.8 to 2.1 ppm: u.c.: 11 H 2.6 ppm: DMSO 3.4 ppm: DHO 3.8 ppm: s: 3 H 3.95 ppm: d: 1 H 8.6 ppm: bs: 3 H.

EXAMPLE 1

2-[5-(2,6-Dimethoxyphenyl)-1-(4-formamido-1-naphthyl)-3-pyrazolylcarbonylamino]-2-adamantanecarboxylic Acid (I: R=—NHCHO; T=Me; AA(OH)=2-carboxy-2-adamantyl)

A) 5-(2,6-Dimethoxyphenyl)-1-(4-nitro-1-naphthyl)-3-pyrazolecarbonyl Chloride

A solution of 14.6 g of the acid prepared in Preparation 4.1 in 100 ml of DCM and 30 ml of thionyl chloride are heated to reflux for 4 hours. The mixture is evaporated under vacuum, the residue is taken up with DCM and the mixture is evaporated again. The acid chloride thereby obtained is used in the next step without further treatment.

B) 2-[5-(2,6-Dimethoxyphenyl)-1-(4-nitro-1-naphthyl)-3-pyrazolylcarbonylamino]-2-adamantanecarboxylic Acid (I': R'=—NO$_2$; T=Me; AA(OH)=2-carboxy-2-adamantyl)

A solution of acid chloride prepared in the preceding step in 20 ml of DCM is added at RT to a suspension of 6.8 g of 2-amino-2-adamantanecarboxylic acid in 100 ml of DMF and 20 ml of pyridine. The mixture is left stirring overnight at RT and the solvents are evaporated off under vacuum. The residue is taken up with 200 ml of 1N HCl and the precipitate formed is filtered off. 10 g of the expected product are obtained after two successive recrystallizations in MeCN, m.p.=268° C.

C) 2-[1-(4-Amino-1-naphthyl)-5-(2,6-dimethoxyphenyl)-3-pyrazolylcarbonylamino]-2-adamantanecarboxylic Acid (I': R'=—NH$_2$; T=Me; AA(OH)=2-carboxy-2-adamantyl)

A mixture of 0.2 g of the compound prepared in the preceding step and 0.05 g of 10% palladium on charcoal in 200 ml of EtOH is hydrogenated at RT for 4 hours at atmospheric pressure. The reaction mixture is filtered and the solvent is evaporated off under vacuum. 0.15 g of the expected product is obtained after crystallization in iso ether and recrystallization in MeOH, m.p.=222° C.

D) 2-[5-(2,6-Dimethoxyphenyl)-1-(4-formamido-1-naphthyl)-3-pyrazolylcarbonylamino]-2-adamantanecarboxylic Acid A mixture of 0.2 g of the compound prepared in the preceding step with 1 ml of formic acid (99–100%; d=1.22) in 2 ml of acetic anhydride is stirred at RT for 1 hour. The reaction mixture is filtered and the solid collected is washed with iso ether. 0.17 g of the expected product is obtained after drying under vacuum at 100° C., m.p.=270° C.

EXAMPLE 2

2-{5-(2,6-Dimethoxyphenyl)-1-[4-(methylsulphonamido)-1-naphthyl]-3-pyrazolylcarbonylamino}-2-adamantanecarboxylic Acid (I: R=—NHSO$_2$Me; T=Me; AA(OH)=2-carboxy-2-adamantyl)

A mixture of 0.3 g of the compound prepared in step C of Example 1, 0.3 g of trimethylsilyl chloride and 1.6 ml of triethylamine in 30 ml of THF is stirred at RT for 1 hour. 0.09 ml of methanesulphonyl chloride is added and the mixture is heated to reflux for 23 hours 30 minutes. It is evaporated under vacuum, the residue is extracted with DCM, and the organic phase is washed with 1N HCl and with water, dried over sodium sulphate and evaporated under vacuum. The product is chromatographed on silica, eluting with DCM and then with a DCM/MeOH (97:3; v/v to 88:12; v/v) mixture. 0.15 g of the expected product is obtained, m.p.=200° C. (dec.).

EXAMPLE 3

2-[1-(4-Acetamido-1-naphthyl)-5-(2,6-dimethoxyphenyl)- 3-pyrazolylcarbonylamino]-2-adamantanecarboxylic Acid (I: R=—NHCOMe; T=Me, AA(OH)=2-carboxy-2-adamantyl)

A) 2-[1-(4-Acetamido-1-naphtyl-5-(2,6-dimethoxyphenyl)-3-pyrazolyl]spiro[adamantane-2,4'-(2'-oxazolin-5'-one)]

A mixture of 0.2 g of the compound prepared in step C of EXAMPLE 1 with 6 ml of acetic anhydride is stirred at RT for 50 minutes. The mixture is evaporated under vacuum and the residue is taken up with 5% aqueous sodium carbonate solution. The precipitate is filtered off, washed with water and dried in a desiccator. The product is chromatographed on silica H, eluting with a DCM/AcOEt (95:5; v/v) mixture. 0.093 g of the expected product is obtained after crystallization in iso ether, m.p.=213° C. (dec.).

B) 2-[1-(4-Acetamido-1-naphthyl)-5-(2,6-dimethoxyphenyl)- 3-pyrazolylcarbonylamino)-2-adamantanecarboxylic Acid A solution of 0.09 g of the compound prepared in the preceding step in 2 ml of TFA and 2 ml of DCM is left at RT for 15 days. The solvents are evaporated off under vacuum and the residue is taken up with ether. 0.065 g of the expected product is obtained after filtration and washing with ether, m.p.=213° C. (dec.).

EXAMPLE 4

2-{5-(2,6-Dimethoxyphenyl)-1-[4-(ethanecarboxamido)- 1-naphthyl]-3-pyrazolylcarbonylamino}-2-adamantanecarboxylic Acid (I: R=—NHCOEt; T=Me; AA(OH)=2-carboxy-2-adamantyl)

A solution of 0.14 g of 2-amino-2-adamantanecarboxylic acid and 0.3 ml of bis(trimethylsilyl)acetamide in 7 ml of MeCN is heated to reflux for 2 hours 30 minutes under a nitrogen atmosphere. The mixture is stored at RT. Separately, 0.1 ml of isobutyl chloroformate is added to a solution, cooled to +5° C., 0.31 g of the compound prepared in Preparation 4.2 and 0.1 ml of triethylamine in 5 ml of DCM. The mixture is stirred for 3 hours at RT. This solution is poured into the above solution of the silyl derivative and left for 4 days at RT under a nitrogen atmosphere. The mixture is acidified-to pH 1 by adding 1N HCl and extracted with DCM, and the organic phase is dried over sodium sulphate and evaporated under vacuum. The residue is taken up in cyclohexane under reflux and, after settling has taken place, the product is extracted with iso ether under reflux. 0.15 g of the expected product is obtained after crystallization on cooling to RT, m.p.=192° C.

EXAMPLE 5

2-[1-(4-Cyano-1-naphthyl)-5-(2,6-dimethoxyphenyl)-3-pyrazolylcarbonylamino]-2-adamantanecarboxylic Acid (I: R=—CN; T=Me; AA(OH)=2-carboxy-2-adamantyl)

A) 1-(4-Cyano-1-naphthyl)-5-(2,6-dimethoxyphenyl)-3-pyrazolecarbonyl Chloride

This compound is prepared according to the procedure described in step A of EXAMPLE 1, from 0.5 g of the compound obtained in Preparation 4.3 and 0.32 ml of thionyl chloride. 0.47 g of expected product is obtained, and it is used in the next step without further treatment.

B) 2-[1-(4-Cyano-1-naphthyl)-5-(2,6-dimethoxyphenyl)-3-pyrazolylcarbonylamino]-2-adamantanecarboxylic Acid This compound is prepared according to the procedure described in step B of EXAMPLE 1, from 0.47 g of the acid chloride of the preceding step and 0.25 g of 2 -amino-2-adamantanecarboxylic acid. After evaporation under vacuum, the residue is taken up with DCM and the precipitate formed is filtered off. The product is chromatographed on silica H, eluting with a DCM/AcOEt/AcOH (95:4.5:0.5; v/v/v) mixture. 0.152 g of the expected product is obtained after crystallization in ether, m.p.=290° C.

EXAMPLE 6

2-{1-[4-(Hydroxyiminocarboxamido)-1-naphthyl]-5-( 2,6-dimethoxyphenyl)-3-pyrazolylcarbonylamino}-2-adamantanecarboxylic Acid (I: R = —C—NH$_2$; T = Me; AA(OH) = 2-carboxy-2-adamantyl)
$\phantom{(I: R = }\|$
$\phantom{(I: R = }$NOH A solution of 0.2 g of hydroxylamine hydrochloride in 10 ml of MeOH is added to a solution of 0.2 g of the compound prepared in EXAMPLE 5 in 20 ml of EtOH; a solution of 0.2 g of potassium carbonate in 4 ml of water is then introduced. The reaction mixture is heated to reflux for 2 days and then partially concentrated under vacuum. 0.15 g of the expected product is obtained after adding water and filtering off the precipitate formed, m.p.=230° C.

EXAMPLE 7

2-[1-(4-Carbamoyl-1-naphthyl)-5-(2,6-dimethoxyphenyl)- 3-pyrazolylcarbonylamino]-2-adamantanecarboxylic Acid (I: R=—CONH$_2$; T=Me; AA(OH)=2-carboxy-2-adamantyl)

A mixture of 0.2 g of the compound prepared in EXAMPLE 5, 0.4 ml of hydrogen peroxide (33% aqueous solution) and 0.4 ml of 6N NaOH in 25 ml of 95% EtOH is heated to reflux for 2 days. 0.4 ml of hydrogen peroxide and 0.4 ml of 6N NaOH are then added to the reaction mixture and refluxing is continued for 1 day. After filtration, the filtrate is diluted with water and extracted with DCM. The aqueous phase is acidified to pH 2 by adding concentrated HCl. The precipitate formed is filtered off and washed with water. 0.128 g of the expected product is obtained after crystallization, m.p.=287° C.

The compound of EXAMPLE 7 may also be obtained according to the process described below.

2-[1-(4-Carbamoyl-1-naphthyl)-5-(2,6-dimethoxyphenyl)-3-pyrazolylcarbonylamino]-2-adamantanecarboxylic Acid This compound is prepared according to the procedure described in EXAMPLE 4, from 0.45 g of the compound obtained in Preparation 4.4 and 0.22 g of 2 -amino-2-adamantanecarboxylic acid. The compound is purified by chromatography on silica, eluting with a DCM/MeOH/

AcOH (100:4:0.5; v/v/v) mixture followed by crystallization in ether. 0.3 g of the expected product is obtained, m.p.=292° C.

EXAMPLE 8

Sodium 2-[1-(4-carbamoyl-1-naphthyl)-5-(2,6-dimethoxyphenyl)- 3-pyrazolylcarbonylamino)-2-adamantanecarboxylate (I: R=—CONH$_2$; T=Me; AA(OH)=2-carboxy-2-adamantyl, Sodium Salt)

0.05 g of the compound prepared in EXAMPLE 7 is added to a solution of 0.005 g of sodium carbonate in 0.3 ml of water and 3 ml of MeOH. The mixture is left for 48 hours at −18° C. After evaporation to dryness under vacuum, the residue is triturated in 3 ml of 2-propanol. 0.04 g of the expected product is obtained after filtration and drying under vacuum over P$_2$O$_5$, m.p.=335° C. (dec.).

EXAMPLE 9

N-Methyl-D-glucamine 2-[1-(4-carbamoyl-1-naphthyl)- 5-(2,6-dimethoxyphenyl)-3-pyrazolylcarbonylamino]-2-adamantanecarboxylate (I: R=—CONH$_2$; T=Me; AA(OH)=2-carboxy-2-adamantyl, N-methyl-D-glucamine Salt)

0.05 g of the compound prepared in EXAMPLE 7 is added to a solution of 0.017 g of N-methyl-D-glucamine in 4 ml of MeOH; 8 ml of ether are then added. The mixture is left for 3 days at −18° C. 0.04 g of the expected product is obtained after filtering off the crystals formed and drying under vacuum over P$_2$O$_5$, m.p.=170°–172° C.

EXAMPLE 10

(2S)-2-[1-(4-Carbamoyl-1-naphthyl)-5-(2,6-dimethoxyphenyl)- 3-pyrazolylcarbonylamino]-2-cyclohexylacetic Acid (I: R=—CONH$_2$; T=Me; AA(OH)=α-carboxycyclohexylmethyl)

A) (2S)-2-[1-(4-Carbamoyl-1-naphthyl)-5-(2,6-dimethoxyphenyl)- 3-pyrazolylcarbonylamino]-2-cyclohexylacetic Acid Methyl Ester (I: R=—CONH$_2$; T=Me; AA(OH)=α-carboxycyclohexylmethyl Methyl Ester)

A mixture of 0.45 g of the compound obtained in Preparation 4.4, 0.15 ml of triethylamine and 0.15 ml of isobutyl chloroformate in 10 ml of DCM is stirred at RT for 1 hour 30 minutes under a nitrogen atmosphere. A solution of 0.224 g of (S)-cyclohexylglycine methyl ester hydrochloride and 0.15 ml of triethylamine in 5 ml of DCM is then added slowly. The mixture is left stirring for 5 days at RT. After filtering off some insoluble matter, the filtrate is washed with 1N HCl solution, dried over sodium sulphate and evaporated under vacuum. 0.37 g of the expected product is obtained after recrystallization in MeCN, m.p.=198° C.

B) (2S)-2-[1-(4-Carbamoyl-1-naphthyl)-5-(2,6-dimethoxyphenyl)- 3-pyrazolylcarbonylamino]-2-cyclohexylacetic Acid A solution of 0.081 g of KOH in 1 ml of water is added at RT to a solution of 0.33 g of the compound obtained in the preceding step in 5 ml of dioxane, and the reaction mixture is left stirring for 5 hours at RT. It is then evaporated under vacuum and the residue is taken up with water. It is acidified to pH 1 by adding 1N HCl solution. 0.28 g of the expected product is obtained after filtration, washing with water and drying, m.p.=186° C. α$_D$=+4° (c=0.5; EtOH).

EXAMPLE 11

2-{1-[4-(Acetylaminomethyl)-1-naphthyl]-5-(2,6-dimethoxyphenyl)- 3-pyrazolylcarbonylamino}-2-adamantanecarboxylic Acid (I: R=—CH$_2$NHCOMe; T=Me; AA(OH)=2-carboxy-2-adamantyl)

A) 1-[4-(Acetylaminomethyl)-1-naphthyl]-5-(2,6-dimethoxyphenyl)- 3-pyrazolecarbonyl Chloride This compound is prepared according to the procedure described in step A of EXAMPLE 1, from 0.55 g of the compound obtained in Preparation 4.5 and 0.31 ml of thionyl chloride. The product obtained is used in the next step without further treatment.

B) 2-{1-[4-(Acetylaminomethyl)-1-naphthyl]-5-(2,6-dimethoxyphenyl)- 3-pyrazolylcarbonylamino}-2-adamantanecarboxylic Acid A solution of the acid chloride prepared in the preceding step in 7 ml of DCM is added at RT under a nitrogen atmosphere to a mixture of 0.29 g of 2-amino-2-adamantanecarboxylic acid and 15 ml of pyridine. The resulting mixture is left stirring for 72 hours at RT. Some insoluble matter is then filtered off and the filtrate is evaporated under vacuum. The residue is extracted with DCM, the organic phase is washed with a pH 2 buffer and dried over sodium sulphate and the solvent is evaporated off under vacuum. The product is then chromatographed on silica H, eluting with a DCM/MeOH (100:4; v/v) mixture. 0.15 g of the expected product is obtained after crystallization in ether, m.p.=211° C.

EXAMPLE 12

2-{5-(2,6-Dimethoxyphenyl)-1-[4-(dimethylaminosulphonyl)- 1-naphthyl]-3-pyrazolylcarbonylamino}-2-adamantanecarboxylic Acid (I: R=—SO$_2$N(Me)$_2$; T=Me; AA(OH)=2-carboxy-2-adamantyl).

A) 5-(2,6-Dimethoxyphenyl)-1-[4-(dimethylaminosulphonyl)- 1-naphthyl]-3-pyrazolecarbonyl Chloride This compound is prepared according to the procedure described in step A of EXAMPLE 1, from 1.46 g of the compound obtained in Preparation 4.6 and 0.77 ml of thionyl chloride. The product obtained is used immediately in the next step.

B) 2-{5-(2,6-Dimethoxyphenyl)-1-[4-(dimethylaminosulphonyl)- 1-naphthyl]-3-pyrazolylcarbonylamino}-2-adamantanecarboxylic Acid This compound is prepared according to the procedure described in step B of EXAMPLE 11, from the compound obtained in the preceding step and 0.7 g of 2- -amino-2-adamantanecarboxylic acid. The product is purified by chromatography on silica H, eluting with a DCM/AcOEt/AcOH (90:10:0.5; v/v/v) mixture. 0.6 g of the expected product is obtained after crystallization in hexane, m.p.=269° C.

EXAMPLE 13

2-{5-(2,6-dimethoxyphenyl)-1-[4-{N-methyl-N-[3 -(N',N'-dimethylamino)propyl]aminosulphonyl}-1-naphthyl]-3-pyrazolylcarbonylamino}-2-adamantanecarboxylic Acid Hydrochloride (I: R=—SO$_2$N(Me)(CH$_2$)$_3$N(Me)$_2$; T=Me; AA (OH)=2-carboxy-2-adamantyl)

This compound is prepared according to the procedure described in EXAMPLE 4 from 0.37 g of the compound obtained in Preparation 4.7 and 0.13 g of 2-amino-2-adamantanecarboxylic acid. The product is purified by chromatography on silica H, eluting with a DCM/MeOH/AcOH (100:8:1; v/v/v) mixture. 0.11 g of the expected product is obtained after crystallization in ether, m.p.=246° C. (dec.).

The compound of EXAMPLE 13 may also be obtained according to the 2 steps of the process described below.
A') 5-(2,6-Dimethoxyphenyl)-1-[4-{N-methyl-N-[3-(N',N'-dimethylamino)propyl]aminosulphonyl}-1-naphthyl]-3-pyrazolecarbonyl Chloride A mixture of 0.2 g of the compound obtained in Preparation 4.7 and 2 ml of thionyl chloride is stirred for 3 hours under a nitrogen atmosphere at RT. A further 2 ml of thionyl chloride are then added and stirring is continued at RT for 1 hour 30 minutes. The reaction mixture is evaporated under vacuum, the residue is taken up with DCM and the mixture is evaporated again under vacuum. The acid chloride thereby obtained is used in the next step without further treatment.
B') 2-{5-(2,6-Dimethoxyphenyl)-1-[4-{N-methyl-N-[3-(N',N'-dimethylamino)propyl]aminosulphonyl}-1-naphthyl]-3-pyrazolylcarbonylamino}-2-adamantanecarboxylic Acid A mixture of 0.071 g of 2-amino-2-adamantanecarboxylic acid and 0.36 ml of bis(trimethylsilyl)acetamide in 10 ml of MeCN is heated to reflux for 15 minutes under a nitrogen atmosphere. After cooling, a solution of the acid chloride obtained in the preceding step in 10 ml of DCM is added and the mixture is left stirring for 48 hours at RT. Water is added, the mixture is acidified to pH 2 by adding 1.2N HCl and extracted with DCM, and the organic phase is dried over sodium sulphate and evaporated under vacuum. 0.23 g of the expected product is obtained.

EXAMPLE 14

2-{1-[4-(Carbamoylmethyl)-1-naphthyl]-5-(2,6-dimethoxyphenyl)-3-pyrazolylcarbonylamino}-2-adamantanecarboxylic Acid (I: R=—CH$_2$CONH$_2$; T=Me; AA(OH)=2-carboxy-2-adamantyl)

This compound is prepared according to the procedure described in EXAMPLE 4, from 0.8 g of the compound obtained in Preparation 4.8 and 0.4 g of 2-amino-2-adamantanecarboxylic acid. After evaporation of the reaction mixture, 1N HCl solution and EtOH are added to the residue. After stirring, the precipitate formed is filtered off and dried under vacuum. The product is then chromatographed on silica H, eluting with a DCM/MeOH/AcOH (100:4:0.5; v/v/v) mixture. The product obtained is dissolved in a solution of 1N NaOH and EtOH, the mixture is acidified to pH 1 by adding 1N HCl and extracted with DCM, the organic phase is dried over sodium sulphate and the solvent is evaporated off under vacuum. 0.53 g of the expected product is obtained after crystallization in EtOH, m.p.=224° C.

EXAMPLE 15

2-{1-[4-(Carboxymethyl)-1-naphthyl]-5-(2,6-dimethoxyphenyl)-3-pyrazolylcarbonylamino}-2-adamantanecarboxylic Acid (I: R=—CH$_2$CO$_2$H; T=Me; AA(OH)=2-carboxy-2-adamantyl)

A mixture of 0.17 g of the compound obtained in EXAMPLE 14 and 0.135 g of sodium peroxide in 5 ml of water and a few drops of MeOH is heated to 60° C. for 1 day. The mixture is acidified to pH 1 by adding 1N HCl and left stirring. After filtration, the expected product is obtained by crystallization in MeCN, m=0.1 g, m.p.=267° C.

EXAMPLE 16

2-[5-(2,6-Dimethoxyphenyl)-1-{4-[3-(N,N-dimethylamino)propoxy]-1-naphthyl}-3-pyrazolylcarbonylamino]-2-adamantanecarboxylic Acid (I: R=—O(CH$_2$)$_3$N(Me)$_2$; T=Me; AA(OH)=2-carboxy-2-adamantyl)

This compound is prepared according to the procedure described in EXAMPLE 4, from 0.19 g of the compound obtained in Preparation 4.9 and 0.14 g of 2-amino-2-adamantanecarboxylic acid. The compound is purified by chromatography on silica, eluting with a DCM/MeOH/NH$_4$OH (100:15:1; v/v/v) mixture. 0.04 g of the expected product is obtained, m.p.=200° C.

EXAMPLE 17

2-{1-[4-(Carbamoylmethoxy)-1-naphthyl]-5-(2,6-dimethoxyphenyl)-3-pyrazolylcarbonylamino}-2-adamantanecarboxylic Acid (I: R=—OCH$_2$CONH$_2$; T=Me; AA(OH)=2-carboxy-2-adamantyl)

This compound is prepared according to the procedure described in EXAMPLE 4, from 0.31 g of the compound obtained in Preparation 4.10 and 0.27 g of 2-amino-2-adamantanecarboxylic acid. The compound is purified by chromatography on silica H, eluting with a DCM/MeOH/AcOH (100:1:0.5; v/v/v) mixture. 0.14 g of expected product is obtained, m.p.=200° C.

EXAMPLE 18

2-{5-(2,6-Dimethoxyphenyl)-1-[4-{N-[3-(N',N'-dimethylamino)propyl]carbamoyl}-1-naphthyl]-3-pyrazolylcarbonylamino}-2-adamantanecarboxylic Acid (I: R=—CONH(CH$_2$)$_3$N(Me)$_2$; T=Me; AA(OH)=2-carboxy-2-adamantyl)

A mixture of 2 g of the compound obtained in Preparation 4.11 and 10 ml of thionyl chloride in 30 ml of DCM is heated to 35° C. for 1 hour. The mixture is concentrated under vacuum and the acid chloride thereby obtained is used without further treatment. Separately, a mixture of 1.2 g of 2-amino-2-adamantanecarboxylic acid and 3 ml of bis(trimethylsilyl)acetamide in 70 ml of MeCN is heated to reflux for 1 hour. After cooling to RT, a solution of the acid chloride prepared above in 50 ml of DCM is added, followed by 0.57 ml of triethylamine, and the reaction mixture is left stirring for 48 hours at RT. It is concentrated under vacuum, the residue is taken up with water, the mixture is acidified to pH 2 by adding 1N HCl and left stirring for 1 hour, and the precipitate formed is drained. The precipitate is dissolved in hot water, 5% NaOH solution is added to pH 6, the mixture is extracted with DCM, the organic phase is dried over Na$_2$SO$_4$ and the solvent is evaporated off under vacuum. 0.48 g of the expected product is obtained after crystallization in 2-propanol and recrystallization in MeOH, m.p.= 244° C.

NMR spectrum at 200 MHz in DMSO: 1.4 to 2.1 ppm: u.c.: 14 H 2.2 ppm: s: 6 H 2.4 ppm: t: 2 H 2.55 ppm: u.c.: 2 H 3.4 ppm: qr: 2 H 3.6 ppm: s: 6 H 6.5 ppm: d: 2 H 6.9 ppm: s: 1 H 7.2 ppm: t: 1 H 7.4to7.8ppm: u.c.:6 H 8.2 ppm: u.c.: 1 H 8.7 ppm: t: 1 H.

EXAMPLE 19

2-{5-(2,6-Dimethoxyphenyl)-1-[4-{N-[3-(N',N'-dimethylamino)propyl]carbamoyl}-1-naphthyl]-3-pyrazolylcarbonylamino}-2-adamantanecarboxylic Acid P-toluenesulphonate 0.130 ml of isobutyl chloroformate is added to a solution, cooled to +5° C., of 0.4 g of the compound obtained in Preparation 4.11 and 0.127 ml of triethylamine in 10 ml of DCM, and the mixture is left stirring for 2 days at RT. Separately, a mixture of 0.231 g of 2-amino-2-adamantanecarboxylic acid and 0.87 ml of bis(trimethylsilyl)acetamide in 15 ml of MeCN is heated to reflux for 1 hour 30 minutes. After cooling to RT, the solution of mixed anhydride prepared above is added and the mixture is left stirring for 2 days at RT. Water is added to the reaction mixture, which is acidified to pH 2 by adding 1N HCl, left stirring and concentrated under vacuum. The residue is taken up with water, 5% NaOH solution is added to pH 6.5, the mixture is extracted with DCM, some insoluble matter is filtered off, the filtrate is dried over $Na_2SO_4$ and the solvent is evaporated off under vacuum. 0.23 g of crude product is obtained. 0.11 g of the product thereby obtained is dissolved in a minimum of MeCN, 0.032 g of p-toluenesulphonic acid monohydrate is added and ether is added until precipitation occurs. 0.050 g of the expected product is obtained after draining and drying.

NMR spectrum at 200 MHz in DMSO: 1.6 to 2.2 ppm: u.c.: 14 H 2.4 ppm: s: 3 H 2.5 ppm: u.c.: 2 H 2.9 ppm: s: 6 H 3.2 ppm: t: 2 H 3.3 to 3.8 ppm: u.c.: 8 H 6.5 ppm: d: 2 H 6.9 ppm: s: 1 H 7.2 ppm: d: 3 H 7.4 to 7.8 ppm: u.c.: 7 H 8.2 ppm: u.c.: 1 H 8.7 ppm: t: 1 H.

EXAMPLE 20

2-{5-(2,6-Dimethoxyphenyl)-1-[4-{N-[2-(N',N'-dimethylamino)ethyl]carbamoyl}-1-naphthyl]-3-pyrazolylcarbonylamino}-2-adamantanecarboxylic Acid (I: R=—CONH(CH$_2$)$_2$N(Me)$_2$; T=Me; AA(OH)=2-carboxy-2-adamantyl)

A mixture of 2 g of the compound obtained in Preparation 4.12 and 10 ml of thionyl chloride in 30 ml of DCM is heated to 35° C. for 1 hour. The mixture is concentrated under vacuum and the acid chloride thereby obtained is used without further treatment. Separately, a mixture of 1.2 g of 2-amino-2-adamantanecarboxylic acid and 3 ml of bis(trimethylsilyl)acetamide in 70 ml of MeCN is heated at reflux for 1 hour. After cooling to RT, a solution of the acid chloride prepared above in 50 ml of DCM is added, followed by 0.58 ml of triethylamine, and the reaction mixture is left stirring overnight at RT. It is concentrated under vacuum, the residue is taken up with water (crystallization of the product), and the mixture is acidified to pH 2 by adding 1N HCl and left stirring for 1 hour. The crystallized product is drained and, after drying, it is chromatographed on silica H, eluting with a gradient of a DCM/MeOH/H$_2$O (100:5:0.2; v;v/v to 100:10:0.75; v/v/v) mixture. 0.62 g of the expected product is obtained after crystallization in acetone.

NMR spectrum at 200 MHz in DMSO: 1.4 to 2.2 ppm: u.c.: 12 H 2.6ppm: u.c:2 H 2.8 ppm: s: 6 H 3.3 ppm: t: 2 H 3.45 ppm: s: 6 H 3.7 ppm: t: 2 H 6.4 ppm: d: 2 H 6.9 ppm: s: 1 H 7.2 ppm: t: 1 H 7.4 ppm: d: 1 H 7.6 ppm: u.c.: 3 H 7.7 ppm: d: 1 H 8.2 ppm: u.c.: 1 H 8.4 ppm: t: 1 H.

This compound is also prepared according to the procedure described below.

0.139 ml of isobutyl chloroformate is added to a solution, cooled to +5° C., of 0.44 g of the compound obtained in Preparation 4.12 and 0.140 ml of triethylamine in 10 ml of DCM, and the mixture is left stirring for 3 days at RT.

Separately, a mixture of 0.321 g of 2-amino-2-adamantanecarboxylic acid and 0.49 ml of bis(trimethylsilyl)acetamide in 20 ml of MeCN is heated to reflux for 1 hour 30 minutes. After cooling to RT, the solution of mixed anhydride prepared above is added and the mixture is left stirring for 3 days at RT. 1N HCl solution is added to pH 2, followed by MeOH, and the mixture is concentrated under vacuum. The residue is taken up with saturated NaCl solution, the mixture is extracted with DCM, the organic phase is dried over $Na_2SO_4$ and the solvent is evaporated off under vacuum. The residue is taken up with water, aqueous ammonia solution is added to pH 7–8, and the precipitate formed is drained and dried. The precipitate is chromatographed on silica H, eluting with a DCM/MeOH/H$_2$O (80:10:0.75; v/v/v) mixture and then with a DCM/MeOH/H$_2$O (80:15:2; v/v/v) mixture. 0.04 g of the expected product is obtained.

EXAMPLE 21

2-[1-{4-[N-(Cyanomethyl)carbamoyl]-1-naphthyl}-5-( 2,6-dimethoxyphenyl)-3-pyrazolylcarbonylamino]-2-adamantanecarboxylic Acid (I: R=—CONHCH$_2$CN; T=Me; AA(OH)=2-carboxy-2-adamantyl)

0.181 ml of isobutyl chloroformate is added to a solution of 0.55 g of the compound obtained in Preparation 4.13 and 0.176 ml of triethylamine in 10 ml of 1,4-dioxane, and the mixture is left stirring for 6 days at RT. Separately, a mixture of 0.351 g of 2-amino-2-adamantanecarboxylic acid and 0.106 ml of bis(trimethylsilyl)acetamide in 20 ml of MeCN is heated to reflux for 1 hour 30 minutes. After cooling to RT, the solution of mixed anhydride prepared above is added and the mixture is left stirring for 3 days at RT. 1N HCl solution is then added to pH 2 and the mixture is left stirring for 2 hours at RT. It is concentrated under vacuum, the residue is taken up with saturated NaCl solution, the mixture is extracted with DCM and some insoluble matter is filtered off. After settling has taken place, the organic phase is dried over $Na_2SO_4$ and the solvent is evaporated off under vacuum. The residue is chromatographed on silica H, eluting with a DCM/MeOH/H$_2$O (80:5:0.3; v/v/v) mixture. 0.080 g of the expected product is obtained.

NMR spectrum at 200 MHz in DMSO: 1.4 to 2.3 ppm: u.c.: 12 H 2.6 ppm: u.c.: 2 H 3.5 ppm: s: 6 H 4.0 ppm: s: 2 H 6.4 ppm: d: 2 H 6.9 ppm: s: 1 H 7.2 ppm: t: 1 H 7.4 to 7.8 ppm: u.c.: 5 H 8.4 ppm: u.c.: 1 H 8.8 ppm: t: 1 H.

EXAMPLE 22

2-[1-{4-[N-(2-Cyanoethyl)-N-methylcarbamoyl]-1-naphthyl}-5-(2,6-dimethoxyphenyl)-3-pyrazolylcarbonylamino]-2-adamantanecarboxylic Acid (I: R=—CON(Me)CH$_2$CH$_2$CN; T=Me; AA(OH)=2-carboxy- 2-adamantyl)

A mixture of 4 g of the compound obtained in Preparation 4.14 and 40 ml of thionyl chloride in 40 ml of DCM is heated to 35° C. for 2 hours. The mixture is concentrated under vacuum and the acid chloride thereby obtained is used without further treatment. Separately, a mixture of 2.34 g of 2-amino-2-adamantanecarboxylic acid and 6 ml of bis(trimethylsilyl)acetamide in 150 ml of MeCN is heated to reflux for 1 hour. After cooling to RT, a solution of the acid chloride prepared above in 100 ml of DCM is added, followed by 1.12 ml of triethylamine, and the mixture is left stirring overnight at RT. It is concentrated under vacuum, the residue is taken up with water, 1N HCl solution is added to pH 2, the mixture is left stirring and the solid formed is drained. After drying, the solid is chromatographed on silica H, eluting with a DCM/MeOH/H$_2$O (100:10:1; v/v/v) mixture. The expected product is obtained after crystallization in acetone, m.p.=264° C.

EXAMPLE 23

2-{5-(2,6-dimethoxyphenyl)-1-[4-{N-methyl-N-[2 -(N$^1$-methyl-N$^2$-methylamidino)ethyl]carbamoyl}-1 -naphthyl]-3-pyrazolylcarbonylamino}-2-adamantanecarboxylic Acid (I: R=—CON(Me)CH$_2$CH$_2$C(=NMe)NHMe; T=Me; AA(OH)= 2-carboxy-2-adamantyl)

1 g of the compound obtained in EXAMPLE 22 is dissolved in 30 ml of EtOH and 10 ml of ether, and gaseous HCl is then bubbled through for 2 hours. The mixture is left overnight at +5° C. and concentrated under vacuum. The residue is taken up in 50 ml of EtOH and gaseous methylamine is bubbled through for 2 hours at RT. The mixture is concentrated under vacuum, the residue is taken up in an EtOH/ether mixture, the methylamine hydrochloride which has crystallized is filtered off and the filtrate is evaporated under vacuum. The residue is taken up with water, and the crystals formed are drained and dried. 0.7 g of the expected product is obtained after recrystallization in EtOH, m.p.= 235° C.

NMR spectrum at 200 MHz in DMSO: 1.4 to 2.4 ppm: u.c.: 12 H 2.5 to 4.0 ppm: u.c.: 21 H 6.5 ppm: d: 2 H 6.9 ppm: s: 1 H 7.15 ppm: t: 1 H 7.3to 7.8ppm: u.c.: 6 H.

EXAMPLE 24

2-{5-(2,6-Dimethoxyphenyl)-1-[4-(N$^1$-methyl-N$^2$ -methylamidino)-1-naphthyl]-3-pyrazolylcarbonylamino}-2-adamantanecarboxylic Acid (I: R=—C(=NMe)NHMe; T=Me; AA(OH)=2-carboxy-2-adamantyl)
A) 2-{5-(2,6-Dimethoxyphenyl)-1-[4-(N-methylcarbamoyl)- 1-naphthyl]-3-pyrazolylcarbonylamino}-2-adamantanecarboxylic Acid This compound is prepared according to the procedure described in EXAMPLE 22, from 2 g of the compound obtained in Preparation 4.15, 25 ml of thionyl chloride and then 1.39 g of 2-amino-2-adamantanecarboxylic acid, 3.5 ml of bis(trimethylsilyl)acetamide and 0.64 ml of triethylamine. The product is chromatographed on silica H, eluting with a DCM/MeOH/H$_2$O (100:3:0.2; v/v/v, then 100/5/0.4; v/v/v) mixture. 1.2 g of the expected product are obtained, m.p.= 170° C.

B) 2-{5-(2,6-Dimethoxyphenyl)-1-[4-(N$^1$-methyl-N$^2$ -methylamidino)- 1-naphthyl]-3-pyrazolylcarbonylamino}-2-adamantanecarboxylic Acid A mixture of 0.5 g of the compound obtained in the preceding step and 0.34 g of phosphorus pentachloride in 15 ml of toluene is heated to reflux for 20 minutes. After cooling, the solid crystallized is drained, the crystals are taken up in 30 ml of EtOH and gaseous methylamine is bubbled into the solution. The mixture is concentrated under vacuum and the residue is chromatographed on silica H, eluting with a DCM/MeOH/H$_2$O (100:2:0.2; v/v/v) mixture. 0.18 g of the expected product is obtained, m.p.=180° C.

EXAMPLE 25

2-{1-[4-(2,6-Acetamidohexanoylamino)-1-naphthyl]- 5-(2,6-dimethoxyphenyl)-3-pyrazolylcarbonylamino}-2-adamantanecarboxylic Acid (I: R=—NHCO(CH$_2$)$_5$NHCOMe; T=Me; AA(OH)=2-carboxy-2-adamantyl)

0.12 ml of isobutyl chloroformate is added to a solution, cooled to 5° C., of 0.4 g of the compound obtained in Preparation 4.16 and 0.2 ml of triethylamine in 5 ml of MeCN, and the mixture is left stirring for 2 hours at RT. Separately, a mixture of 0.21 g of 2-amino-2-adamantanecarboxylic acid and 2 ml of bis(trimethylsilyl)acetamide in 3 ml of MeCN is left stirring for 2 hours at RT. This solution is then added to the solution of mixed anhydride prepared above, and the mixture is left stirring for 16 days at RT. 5 ml of MeOH and 1 ml of water are then added to the reaction mixture, which is left stirring for 30 minutes and concentrated under vacuum. The residue is taken up in 100 ml of DCM, some insoluble matter is filtered off, the filtrate is washed with water and with 1N HCl solution, and the organic phase is dried over Na$_2$SO$_4$ and evaporated under vacuum. The residue is chromatographed on silica H, eluting with a DCM/MeOH/AcOH (100:8:1; v/v/v) mixture. 0.07 g of the expected product is obtained after crystallization in ether, m.p.=190° C.

EXAMPLE 26

2-{1-[4-(2-Aminoethyl)-1-naphthyl]-5-(2,6 -dimethoxyphenyl)-3-pyrazolylcarbonylamino}-2-adamantanecarboxylic Acid (I: R=—CH$_2$CH$_2$NH$_2$; T=Me; AA(OH)=2-carboxy-2-adamantyl)
A) 2-{1-[4-(Cyanomethyl)-1-naphthyl]-5-(2,6-dimethoxyphenyl)- 3-pyrazolylcarbonylamino}-2-adamantanecarboxylic Acid A mixture of 5 g of the compound obtained in Preparation 4.8 and 50 ml of thionyl chloride in 125 ml of DCM is heated to 40° C. for 1 hour and then concentrated under vacuum. Separately, a mixture of 3.38 g of 2-amino- 2-adamantanecarboxylic acid and 8.75 ml of bis(trimethylsilyl)acetamide in 150 ml of MeCN is heated to reflux for 1 hour. After cooling to RT, a solution of the acid chloride prepared above in 100 ml of DCM is added, followed by 1.6 ml of triethylamine, and the mixture is left stirring overnight at RT. It is concentrated under vacuum, the residue is dissolved in EtOH and ether is added until crystallization occurs. After draining of the crystals (compound of EXAMPLE 14), the filtrate is concentrated under vacuum. The residue is taken up in EtOH, 3N HCl solution is added to pH 1, and the precipitate formed is drained and dried. The precipitate is chromatographed on silica H, eluting with a DCM/MeOH/AcOH (100:3:0.5; v/v/v) mixture. The compound of EXAMPLE 14 is separated and 1.2 g of the expected product are then obtained.

B) 2-{1-[4-(2-Aminoethyl)-1-naphthyl]-5-(2,6-dimethoxyphenyl)- 3-pyrazolylcarbonylamino}-2-adamantanecarboxylic Acid A mixture of 1.2 g of the compound obtained in the preceding step, 0.12 g of Raney® nickel, 60 ml of MeOH and 10 ml of concentrated aqueous ammonia is hydrogenated at RT and at atmospheric pressure. The catalyst is filtered off and the filtrate is partially concentrated under vacuum. The crystals formed are drained and dried. 0.89 g of the expected product is obtained, m.p.=250° C.

NMR spectrum at 200 MHz in DMSO: 1.4 to 2.2 ppm: u.c.: 12 H 2.5 ppm: u.c.: 2 H 3.0 to 3.6 ppm: u.c.: 10 H 6.4 ppm: d: 2 H 6.9 ppm: s: 1 H 7.1 ppm: t: 1 H 7.2 to 7.6 ppm: u.c.: 5 H 8.1 ppm: u.c.: 1 H.

EXAMPLE 27

2-{5-(2,6-Dimethoxyphenyl)-1-[4-{N-methyl-N-[3 -(N',N'-dimethylamino)propyl]carbamoyl}-1-naphthyl]-3-pyrazolylcarbonylamino}-2-adamantanecarboxylic Acid Hydrochloride (I: R=—CON(Me)(CH$_2$)$_3$N(Me)$_2$; T=Me; AA(OH)=2 -carboxy-2-adamantyl)

This compound is prepared according to the procedure described in EXAMPLE 18, from 0.32 g of the compound obtained in Preparation 4.17, 2 ml of thionyl chloride, 5 ml of DCM and then 0,185 g of 2-amino-2-adamantanecarboxylic acid, 0.465 ml of bis(trimethylsilyl)acetamide, 10 ml of MeCN and 0.09 ml of triethylamine. The crude product is dissolved in a minimum of EtOH, a saturated solution of HCl in ether is added and the mixture is concentrated under vacuum. 0.1 g of the expected product is obtained after crystallization in ether.

EXAMPLE 28

2-{5-(2,6-Dimethoxyphenyl)-1-[4-{N-methyl-N-[2 -(N',N'-dimethylamino)ethyl]carbamoyl}-1-naphthyl]-3 -pyrazolylcarbonylamino}-2-adamantanecarboxylic Acid Hydrochloride (I: R=—CON(Me)(CH$_2$)$_2$N(Me)$_2$; T=Me; AA(OH)=2 -carboxy-2-adamantyl)

This compound is prepared according to the procedure described in EXAMPLE 18, from 0.31 g of the compound obtained in Preparation 4.18, 2 ml of thionyl chloride, 5 ml of DCM and then 0.185 g of 2-amino-2-adamantanecarboxylic acid, 0.465 ml of bis(trimethylsilyl)acetamide, 10 ml of MeCN and 0.09 ml of triethylamine. The crude product is dissolved in a minimum of EtOH, a saturated solution of HCl in ether is added and the mixture is concentrated under vacuum. 0.08 g of the expected product is obtained after crystallization in ether.

EXAMPLE 29

2-{5-(2,6-Dimethoxyphenyl)-1-[1,3(2H)-dioxo-1H-benz[de]isoquinol-6-yl]-3-pyrazolylcarbonylamino}-2-adamantanecarboxylic Acid

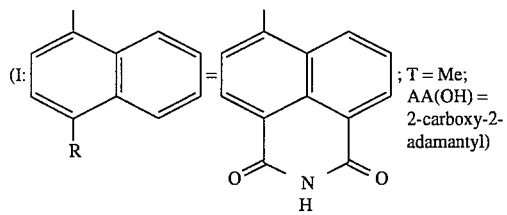

; T = Me; AA(OH) = 2-carboxy-2-adamantyl)

0.43 ml of isobutyl chloroformate is added to a solution, cooled to 5° C., of 1.4 g of the compound obtained in Preparation 4.19 and 0.28 ml of pyridine in 20 ml of MeCN, and the mixture is left stirring for 1 hour at RT. Separately, a mixture of 0.64 g of 2-amino-2-adamantanecarboxylic acid and 1.54 ml of bis(trimethylsilyl)acetamide in 30 ml of MeCN is heated to reflux for 1 hour. After cooling to RT, the solution of mixed anhydride prepared above is added, and the reaction mixture is left stirring for three days at RT and under a nitrogen atmosphere. It is acidified to pH 2 by adding 1N HCl and concentrated under vacuum. The residue is taken up with water, the mixture is extracted with AcOEt, the organic phase is dried over Na$_2$SO$_4$ and the solvent is evaporated off under vacuum. The residue is chromatographed on silica H, eluting with a DCM/MeOH/AcOH (100:1:0.5; v/v/v) mixture. The product obtained is taken up in MeOH, and the mixture is alkalinized by adding concentrated NaOH and concentrated under vacuum. The product is taken up in the form of a sodium salt in MeOH, the mixture is acidified to pH 1 by adding 1N HCl and the precipitate formed is drained. 0.17 g of the expected product is obtained, m.p.=210° C.

EXAMPLE 30

2-{5-(2,6-Dimethoxyphenyl)-1-[2-acetamido-1, 3(2H)-dioxo- 1H-benz[de]isoquinol-6-yl]-3-pyrazolylcarbonylamino}-2-adamantanecarboxylic Acid

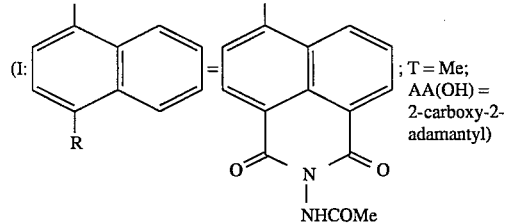

; T = Me; AA(OH) = 2-carboxy-2-adamantyl)

This compound is prepared according to the procedure described in EXAMPLE 29, from 0.9 g of the compound obtained in Preparation 4.21, 0.25 ml of triethylamine, 0.25 ml of isobutyl chloroformate and 15 ml of DCM, and then 0.36 g of 2-amino-2-adamantanecarboxylic acid, 0.89 ml of bis(trimethylsilyl)acetamide and 20 ml of MeCN. The crude product is chromatographed on silica H, eluting with a DCM/MeOH/AcOH (100:3:0.5; v/v/v) mixture. The product obtained is dissolved in 1N NaOH, the mixture is acidified to pH 3 by adding 1N HCl and extracted with AcOEt, the organic phase is dried over Na$_2$SO$_4$ and the solvent is evaporated off under vacuum, 0.45 g of the expected product is obtained after crystallization in ether, m.p.=292° C.

Using the procedure described in EXAMPLE 7 (2nd process), and starting from the compound obtained in Preparation 4.4, the compounds according to the invention collated in TABLE 1 below are prepared.

TABLE 1

[Structure: 5-(2-methoxyphenyl with CH3O)-1-(4-carbamoyl-naphthalen-1-yl)-pyrazole-3-carboxamide with CO—NH—AA(OH)]

| EXAMPLES | —NH—AA(OH) |
|---|---|
| 31 | —HN—(cyclohexyl)—COOH |
| 32 | —HN—(norbornyl)—COOH |
| 33 | —HN—(cyclopentyl)—COOH |
| 34 | —HN—(bicyclic)—COOH |

Using the procedure described in EXAMPLE 10, and starting from the compound obtained in Preparation 4.4, the compounds according to the invention collated in TABLE 2 below are prepared.

TABLE 2

[Structure: 5-(2,6-dimethoxyphenyl)-1-(4-carbamoyl-naphthalen-1-yl)-pyrazole-3-carboxamide with CO—NH—AA(OH)]

| EXAMPLES | —NH—AA(OH) |
|---|---|
| 35 | —HN—CH(CH$_2$—CH(CH$_3$)$_2$)—COOH |
| 36 | —HN—CH((CH$_2$)$_3$—CH$_3$)—COOH |

TABLE 2-continued

[Same structure as above]

| EXAMPLES | —NH—AA(OH) |
|---|---|
| 37 | —HN—CH(CH(CH$_3$)$_2$)—COOH |
| 38 | —HN—CH(adamantyl)—COOH |
| 39 | —HN—CH(adamantyl)—COOH |

EXAMPLE 40

2-{5-(2,6-dimethoxyphenyl)-1-[4-[N-[3-(N',N'-dimethylamino)propyl]carbamoyl]napht-1-yl]pyrazol-3-ylcarbonylamino}adamantane-2-carboxylic Acid Hydrochloride This compound is prepared according to the procedure described in Example 18, from 5.6 g of the compound obtained In Preparation 4.11, 20 ml of oxalyl chloride and 20 ml of DCM and then 3.4 g of 2-aminoadamantane-2-carboxylic acid, 8.4 ml of MeCN and 1.6 ml of triethylamine. 1.3 g of the expected product is obtained under the form of a base after crystallization in propan-2-ol and recrystallization in MeOH(m.p.=242° C.). 20 mg of the product so obtained is dissolved in a minimum of MeOH, acidified to pH 1 by adding a ether solution saturated with HCl and concentrated under vacuum. The expected hydrochloride is obtained after crystallization in a acetone/pentane mixture; m.p.–200° C. (decomposition).

NMR spectrum at 200 MHz in DMSO: 0.4 to 2.3 ppm: u.c.: 14 H 2.6 ppm: bs: 2 H 2.8 ppm: bs: 6 H 3.15 ppm: bs: 2 H 3.4 ppm: bs: 2 H 3.55 ppm: s: 6 H 6.5 ppm: d: 2H 6.9 ppm: s: 1 H 7.2 ppm: t: 1 H 7.3 to 8.3 ppm: u.c.: 7 H 8.8 ppm: bs: 1 H 10 to 13 ppm: 2 bs: 2 H.

We claim:

1. Compound of formula:

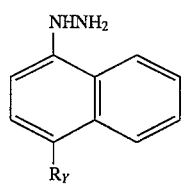
in which:
R_y represents a cyano or carboxymethyl group and its salts.
2. A compound according to claim 1 wherein $R_y$ represents a carboxymethyl group.
* * * * *